(12) United States Patent
Higgs et al.

(10) Patent No.: US 8,729,203 B2
(45) Date of Patent: May 20, 2014

(54) POLYMER COMPOSITION

(76) Inventors: Timothy Charles Higgs, Cambridge (GB); Richard Alexander Young, Linton (GB)

( * ) Notice: Subject to any disclaimer, the term of this patent is extended or adjusted under 35 U.S.C. 154(b) by 0 days.

(21) Appl. No.: 13/319,059

(22) PCT Filed: May 7, 2009

(86) PCT No.: PCT/GB2009/001130
§ 371 (c)(1),
(2), (4) Date: Nov. 4, 2011

(87) PCT Pub. No.: WO2010/128266
PCT Pub. Date: Nov. 11, 2010

(65) Prior Publication Data
US 2012/0053313 A1    Mar. 1, 2012

(51) Int. Cl.
*C08F 12/04* (2006.01)
*C08F 20/38* (2006.01)
*C08F 32/02* (2006.01)

(52) U.S. Cl.
USPC ........ 526/326; 526/286; 526/305; 526/307.2; 568/77

(58) Field of Classification Search
USPC .......................... 526/305, 307.2, 326; 568/77
See application file for complete search history.

(56) References Cited

U.S. PATENT DOCUMENTS

| 3,799,972 | A | 3/1974 | Cawley et al. |
| 4,921,205 | A * | 5/1990 | Drew et al. ..................... 249/61 |
| 5,290,892 | A | 3/1994 | Namdaran et al. |
| 5,403,901 | A | 4/1995 | Namdaran et al. |
| 5,674,960 | A | 10/1997 | Namdaran et al. |
| 5,861,031 | A | 1/1999 | Namdaran et al. |
| 5,922,821 | A | 7/1999 | LeBouef et al. |
| 6,780,899 | B2 | 8/2004 | Liao et al. |
| 2006/0281888 | A1 * | 12/2006 | Schlueter ................. 526/318.44 |
| 2009/0131577 | A1 * | 5/2009 | Kato et al. .................... 524/548 |

FOREIGN PATENT DOCUMENTS

| EP | 1792924 | 6/2007 |
| EP | 1818690 A1 | 8/2007 |
| WO | WO-96/40303 A1 | 12/1996 |
| WO | WO-00/79312 A1 | 12/2000 |
| WO | WO-2007/094664 A1 | 8/2007 |

OTHER PUBLICATIONS

Yurzhenko, T.I.; Vinlenskaya, M.R. "Synthesis of peroxide esters of unsaturated and saturated monobasic acids", 1969, Usp. Khim. Org. Perekisnykh Soedin. Autookisleniy, Dokl. Bses. Kong., 3rd, Meeting Date 1965, p. 64-70.*
International Search Report and Written Opinion of the ISA for International Application No. PCT/GB2009/001130, dated Mar. 17, 2010.
Matsuda et al., Journal of Macromolecular Science, Part A, vol. 36, Issue 9, 1999, pp. 1271-1288. Novel Thiophene Methacrylates for Materials of High Refractive Index.
Vasella et al.; Helvetica Chimica Acta, 1995, vol. 78, pp. 732-757.

* cited by examiner

*Primary Examiner* — Ling Choi
*Assistant Examiner* — David L Miller
(74) *Attorney, Agent, or Firm* — Leyendecker & Lemire, LLC

(57) ABSTRACT

The present invention provides a monomer for a polymerizable composition, a polymerizable composition containing the monomers, a polymer formed from the polymerizable composition, and ophthalmic lens blanks and ophthalmic lenses formed from the polymer. The monomer is a compound having the formula (I) or (Ia).

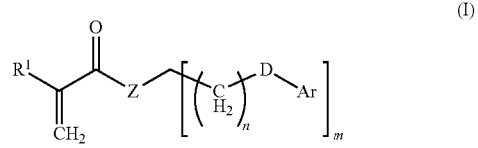

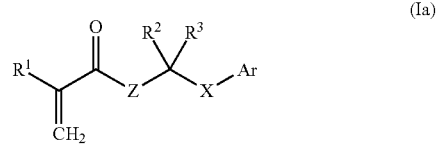

5 Claims, No Drawings

POLYMER COMPOSITION

The present invention relates to a monomer compound, a polymerisable composition containing the monomers, a polymer formed from the polymerisable composition, and ophthalmic lens blanks and ophthalmic lenses formed from the polymer.

Contact and intraocular ophthalmic lenses are devices for correcting defective vision. In particular, it has become commonplace to replace cataractous lenses with intraocular lenses (IOLs) using surgical procedures.

A typical procedure involves fragmenting the patient's cataractous lens by ultrasonic vibration, aspirating the fragmented lens pieces from the patient's eye through an incision in the eye, and then inserting an IOL into the eye through the same incision.

In order to reduce surgical trauma, it is advantageous to minimise the size of the incision. For this reason, foldable IOLs have been developed which can be shaped into a small package for insertion through the incision and which unfold into a final shape after being located in the eye.

A significant class of foldable IOLs are formed from flexible polymers which are capable of unfolding at the temperature of the eye (i.e., about 37° C.) into an appropriate lens shape.

Hydrophobic acrylic-based polymers have been used for forming flexible IOLs of this type, e.g., as disclosed by U.S. Pat. No. 5,674,960, U.S. Pat. No. 5,922,821 and WO 96/40303. Such polymers are rollable and foldable, and have relatively high refractive indices (which enables IOLs to be made thinner without sacrificing optical refractory power). The overall dioptic power of the IOL depends on both the shape of the optic portion of the lens and refractive index of the material from which the lens has been made.

Conventionally, IOLs formed of hydrophobic-acrylic based polymers are produced in a one-step moulding process which gives the IOL its final lens shape. The glass transition temperatures, $T_g$, for the polymers are generally lower than 20° C. so that the IOLs can be folded at room temperature. However, it is not unusual for such low glass transition temperature polymers to exhibit a phenomenon that has been termed as glistenings, whereby a material absorbs a small amount of water, which then accumulates into small pockets. These pockets have a different refractive index to the polymer material and appear to glisten.

Some of the physical properties of the polymer used to make the IOL are dependent on the chemical structure of the monomer. For hydrophobic polymers based on acrylate or methacrylate monomers, the chemical functional group attached to the oxygen atom of the acryl or methacryl ester unit can influence the polymer's physical characteristics. In particular, a chemical functional group, which is known to impart particular physical characteristics to the resulting polymer, is covalently attached to the ester unit of the monomer by a bridging group, such as an alkyl chain.

Many polymers having a relatively high refractive index are based on acrylate or methacrylate monomers containing an aryl functional group with a nearby heteroatom in the bridging group. WO 00/79312 discloses several classes of acrylate or methacrylate based monomers that can be used to form homopolymer or copolymer compositions for the manufacture of IOL implants. These monomers contain an aryl functional group attached to the ester by an alkyl chain bridge. The alkyl bridging group may contain oxygen or sulphur heteroatoms. Several general formulae that represent different classes of acrylate or methacrylate based monomers are disclosed, which cover the following classes of functional group-bridging group units that can be attached to the ester: arylthio-alkyl, aryloxy-alkyl, 3-aryloxy-2-hydroxyalkyl, 3-arylthio-2-hydroxyalkyl, 2-aryloxy-propyl, 2-arylthio-propyl and 2-aryloxy-propyl. The alkyl bridging group is fully saturated or is substituted by a hydroxy or methyl group (i.e. 2-aryloxy-propyl or 2-arylthio-propyl), as indicated by the general names given above.

Copolymers containing phenylthioethyl acrylate (i.e. an acrylate with an arylthio-alkyl side chain) were prepared and tested in WO 00/79312. However, there are no examples of monomers that have a hydroxy or methyl substituent on the alkyl chain that connects the alkoxy oxygen atom of the ester group to the aryloxy or arylthio end groups.

U.S. Pat. No. 5,290,892, U.S. Pat. No. 5,403,901, U.S. Pat. No. 5,674,960 and U.S. Pat. No. 5,861,031 all disclose copolymers based on acrylate or methacrylate monomers. A general formula for acrylate or methacrylate monomers is disclosed which covers the following functional group-bridging group units: phenylthio-alkyl, phenyloxy-alkyl, benzylthio-alkyl and benzyloxy-alkyl. The alkyl bridge and methylene group in the benzyl unit are fully saturated. No examples of polymers containing these monomers are disclosed in these documents.

The present invention is based on the finding that hydrophobic acrylic-based polymers having improved properties can be obtained from a class of acrylate or methacrylate based monomers that have substituents at a particular position on the bridging group.

A first aspect of the present invention provides a monomer for a polymerisable composition, the monomer having the formula (I) or (Ia):

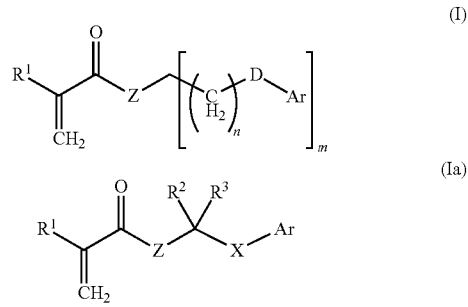

wherein each D is independently:

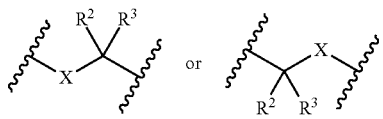

and $R^1$ is hydrogen or a methyl group;
Z is O or N—$R^4$, where $R^4$ is hydrogen or $C_{1-10}$ alkyl;
m is an integer from 1 to 3;
n is an integer from 0 to 6;
$R^2$ and $R^3$ are independently selected from hydrogen, $C_{1-10}$ alkyl, $C_{3-10}$ cycloalkyl, $C_{5-36}$ aryl, $C_{6-37}$ aryl ether, an optionally substituted $C_{4-36}$ heterocyclyl, $C_{1-7}$ alkoxy, $C_{5-36}$ aryloxy, and $C_{2-11}$ alkyl ether, wherein $R^2$ and $R^3$ are not both hydrogen atoms;
X is oxygen or sulphur;
Ar is an optionally substituted $C_{5-36}$ aryl group;

wherein the optional substituents for when Ar is an optionally substituted $C_{5-36}$ aryl group are independently selected from halogen atom, $C_{1-10}$ alkyl, $C_{3-10}$ cycloalkyl, $C_{5-36}$ aryl, $C_{5-37}$ aryl ether, $C_{1-7}$ alkoxy, $C_{6-37}$ aryl thioether, an optionally substituted $C_{4-36}$ heterocyclyl, $C_{2-11}$ alkyl ether, $C_{2-11}$ alkyl thioether, $C_{5-36}$ aryloxy, $C_{5-36}$ arylsulfide, $C_{6-38}$ arylalkyl and an optionally substituted $C_{5-38}$ heterocycyl-alkyl group.

In one embodiment, where m is 2 or 3, each D is the same.

It has been found that the inclusion of a substituent to an alkyl bridging group at a position adjacent to a heteroatom can lead to polymers having a high refractive index and improved stability to degradation.

The heteroatom in the bridging group is generally a more reactive site than the rest of the alkyl chain. If the heteroatom undergoes a chemical reaction, then the character of the side chain is disrupted, which may result in degradation in the polymer's properties. It is believed that the presence of a substituent group adjacent to this particular position shields or provides steric hindrance to other chemical entities that may react with the heteroatom. The presence of a single substituent adjacent to the heteroatom in the bridging group, such as when the functional group is attached to a secondary or branched alkyl chain, is believed to provide additional sterically induced stabilisation over those polymers made from monomers that do not have the substituent. It follows that the sterically induced stabilisation is expected to be increased if there are two substituents at this position.

The number of aryl substituents, Ar, connected to the polymerisable aryl functionality influences the refractive index of the monomer. Thus, the number of "arms" present in the monomer of formula I (determined by the value of m) may be altered to provide a desired refractive index. With one aryl-containing "arm" incorporated into the monomer architecture (i.e. m=1) the refractive index is lower than a molecule having two such "arms" (m=2) which in turn is lower than a monomer having three "arms" (m=3).

As an example, a compound having two arms, i.e. m=2, is shown below:

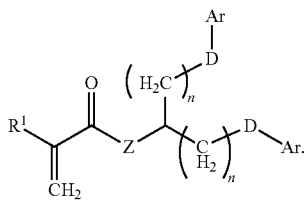

As shown in general formula (I) and (Ia) in the first aspect of the invention, there are two ways of introducing "blocking" substituents onto the bridging group so that they are adjacent to the heteroatom. These are illustrated separately in the formulae (II) and (Ia), and (III) below:

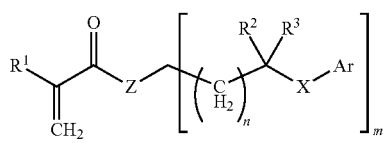
(II)

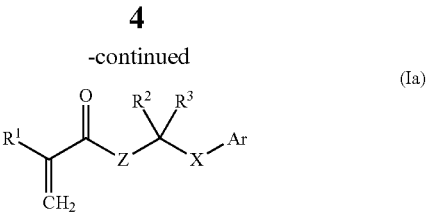
(Ia)

The "blocking" substituents are represented by $R^2$ and/or $R^3$. These can be attached to the alkyl chain bridge adjacent to heteroatom X. Examples of monomers represented by formula (II) include 3-methyl-3-(phenylthio)butyl acrylate, 3-methyl-3-(phenylthio)butyl methacrylate, N-(3-methyl-3-(phenylthio)butyl)acrylamide, N-(3-methyl-3-(phenylthio)butyl)methacrylamide, 3-ethyl-3-(phenylthio)pentyl acrylate, 3-ethyl-3-(phenylthio)pentyl methacrylate, N-(3-ethyl-3-(phenylthio)pentyl)acrylamide, N-(3-ethyl-3-(phenylthio)pentyl)methacrylamide 3-(phenylthio)-3-propylhexyl acrylate, 3-(phenylthio)-3-propylhexyl methacrylate, 3-phenyl-3-(phenylthio)butyl acrylate, 3-phenyl-3-(phenylthio)butyl methacrylate, N-(3-phenyl-3-(phenylthio)butyl)acrylamide, N-(3-phenyl-3-(phenylthio)butyl)methacrylamide, 3,3-diphenyl-3-(phenylthio)propyl acrylate, 3,3-diphenyl-3-(phenylthio)propyl methacrylate, 5-methyl-5-(phenylthio)hexyl methacrylate, 6-methyl-6-(phenylthio)heptyl acrylate, 6-methyl-6-(phenylthio)heptyl methacrylate, N-(6-methyl-6-(phenylthio)heptyl)acrylamide, N-(6-methyl-6-(phenylthio)heptyl)methacrylamide, 7-methyl-7-(phenylthio)octyl acrylate, 7-methyl-7-(phenylthio)octyl methacrylate, 2,6-dimethyl-2,6-bis(phenylthio)heptan-4-yl acrylate, 2,6-dimethyl-2,6-bis(phenylthio)heptan-4-yl methacrylate, N-(2,6-dimethyl-2,6-bis(phenylthio)heptan-4-yl)acrylamide, N-(2,6-dimethyl-2,6-bis(phenylthio)heptan-4-yl)methacrylamide, 2,6-dimethyl-4-(2-methyl-2-(phenylthio)propyl)-2,6-bis(phenylthio)heptan-4-yl acrylate, 2,6-dimethyl-4-(2-methyl-2-(phenylthio)propyl)-2,6-bis(phenylthio)heptan-4-yl methacrylate N-(2,6-dimethyl-4-(2-methyl-2-(phenylthio)propyl)-2,6-bis(phenylthio)heptan-4-yl)acrylamide, N-(2,6-dimethyl-4-(2-methyl-2-(phenylthio)propyl)-2,6-bis(phenylthio)heptan-4-yl)methacrylamide.

An alternative way of introducing a blocking substituent into a bridging group containing a heteroatom is shown below in general formula (III). A substituted methylene group can be introduced between the heteroatom "X" and the "Ar" end group:

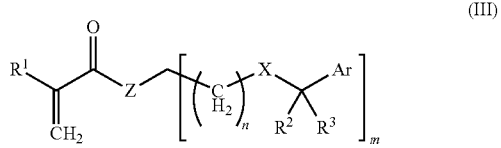
(III)

Examples of monomers represented by formula (III) include 2-(2-phenylpropan-2-ylthio)ethyl acrylate, 2-(2-phenylpropan-2-ylthio)ethyl methacrylate, N-(2-(2-phenylpropan-2-ylthio)ethyl)acrylamide, N-(2-(2-phenylpropan-2-ylthio)ethyl)methacrylamide, 2-(3-phenylpentan-3-ylthio)ethyl acrylate, 2-(3-phenylpentan-3-ylthio)ethyl methacrylate, N-(2-(3-phenylpentan-3-ylthio)ethyl)acrylamide, N-(2-(3-phenylpentan-3-ylthio)ethyl)methacrylamide, 2-(4-phenylheptan-4-ylthio)ethyl methacrylate, N-(2-(4-phenylheptan-4-ylthio)ethyl)acrylamide, N-(2-(4-phenylheptan-4-ylthio)ethyl)methacrylamide, 2-(1,1-diphenylethylthio)ethyl acrylate, 2-(1,1-diphenylethylthio)

ethyl methacrylate, N-(2-(1,1-diphenylethylthio)ethyl)acrylamide, N-(2-(1,1-diphenylethylthio)ethyl)methacrylamide, 2-(tritylthio)ethyl acrylate, 2-(tritylthio)ethyl methacrylate, 3-(2-phenylpropan-2-ylthio)propyl acrylate, 3-(2-phenylpropan-2-ylthio)propyl methacrylate, N-(3-(2-phenylpropan-2-ylthio)propyl)acrylamide, N-(3-(2-phenylpropan-2-ylthio)propyl)methacrylamide, 4-(2-phenylpropan-2-ylthio)butyl acrylate, 4-(2-phenylpropan-2-ylthio)butyl methacrylate, N-(4-(2-phenylpropan-2-ylthio)butyl)acrylamide, N-(4-(2-phenylpropan-2-ylthio)butyl)methacrylamide, 5-(2-phenylpropan-2-ylthio)pentyl acrylate, and 5-(2-phenylpropan-2-ylthio)pentyl methacrylate, 1,5-bis(2-phenylpropan-2-ylthio)pentan-3-yl acrylate, 1,5-bis(2-phenylpropan-2-ylthio)pentan-3-yl methacrylate, N-(1,5-bis(2-phenylpropan-2-ylthio)pentan-3-yl)acrylamide, N-(1,5-bis(2-phenylpropan-2-ylthio)pentan-3-yl)methacrylamide, 1,5-bis(2-phenylpropan-2-ylthio)-3-(2-(2-phenylpropan-2-ylthio)ethyl)pentan-3-yl acrylate, 1,5-bis(2-phenylpropan-2-ylthio)-3-(2-(2-phenylpropan-2-ylthio)ethyl)pentan-3-yl methacrylate, N-(1,5-bis(2-phenylpropan-2-ylthio)-3-(2-(2-phenylpropan-2-ylthio)ethyl)pentan-3-yl)acrylamide, N-(1,5-bis(2-phenylpropan-2-ylthio)-3-(2-(2-phenylpropan-2-ylthio)ethyl)pentan-3-yl)methacrylamide.

Monomer stability is expected to improve as the size of $R^2$ and/or $R^3$ is increased. However, once the size of $R^2$ and/or $R^3$ has reached some limit the sterically induced stabilisation effect may level out. Additional stability may also arise from polymers having improved photostability, whilst maintaining a high refractive index and low $T_g$. The substituents may also protect the heteroatom in the monomer bridging group during polymer formation, including free radical polymerisation.

The following preferences apply to the first aspect of the invention, which includes the monomers represented by formula (I), (Ia), formula (II) and formula (III). The preferences below are also applicable to each of the types of monomer represented by the individual formulae (I), (Ia), (II) or (III).

The first aspect of the invention includes both methacrylate and acrylate based monomers. When $R^1$ is methyl, methacrylate type monomers are represented by formulae (I), (Ia), (II) or (III). Alternatively, when $R^1$ is hydrogen, an acrylate type monomer is represented. Acrylate based monomers, where $R^1$ is hydrogen, are preferred.

In one embodiment, X is O. In one embodiment, X is N—$R^4$.

In one embodiment, $R^2$ and $R^3$ are independently selected from $C_{1-10}$ alkyl, $C_{3-10}$ cycloalkyl, $C_{5-36}$ aryl, $C_{6-37}$ aryl ether, an optionally substituted $C_{4-36}$ heterocyclyl, $C_{1-7}$ alkoxy, $C_{5-36}$ aryloxy and $C_{2-11}$ alkyl ether. Bulkier substituents, such as when $R^2$ or $R^3$ are tert-butyl or adamantyl, are expected to provide more steric protection than smaller substituents. However, the synthesis of monomers containing bulkier substituents may be complicated by the presence of those bulkier groups.

In one embodiment, $R^2$ and $R^3$ are the same.

In one embodiment, $R^2$ and $R^3$ are independently selected from $C_{1-10}$ alkyl and $C_{3-10}$ cycloalkyl.

Where $R^2$ and/or $R^3$ is a $C_{1-10}$ alkyl group, the refractive index of the monomer may be decreased by increasing the number of carbon atoms in the alkyl chain. In one embodiment, at least one of $R^2$ or $R^3$ is $C_{1-10}$ alkyl. In one embodiment, both $R^2$ and $R^3$ are independently $C_{1-10}$ alkyl. In one embodiment, both $R^2$ and $R^3$ are independently selected from methyl, ethyl, n-propyl, i-propyl, n-butyl, s-butyl and t-butyl. In one embodiment, $R^2$ and $R^3$ are both methyl.

In one embodiment, $R^2$ and $R^3$ are independently selected from hydrogen, $C_{1-10}$ alkyl and $C_{3-10}$ cycloalkyl.

In one embodiment, one of $R^2$ and $R^3$ is hydrogen and the other of $R^2$ and $R^3$ is independently selected from $C_{1-10}$ alkyl and $C_{3-10}$ cycloalkyl.

When $R^2$ and $R^3$ are different, the resulting monomer may be optically active. The first aspect of the invention includes optically active monomers that having either of the possible stereochemical configurations i.e. both enantiomeric forms are included of the stereoisomers at this position.

The length of the bridging chain or group in the general formulae (I), (II) or (III) is determined by the size of the integer "n". In one embodiment, n is from 1 to 6. In another embodiment, n has a value from 1 to 4. In one embodiment, n is 1, 2 or 3. In one embodiment, n is 1. In one embodiment, n is 0.

The number of aryl-containing "arms" within the monomer having the general formula (I), (II) or (III) is given by "m". In one embodiment m is 1 or 2. In one embodiment m is 1. Each arm may be the same or different. In one embodiment, the arms are the same.

The group represented by "Ar" may act as a chromophore. Changing the structure of this group can modulate the light absorption properties of the resulting lens polymer.

In one embodiment, Ar is an optionally substituted $C_{5-14}$ aryl group. In one embodiment, Ar is an unsubstituted $C_{5-14}$ aryl group. Example $C_{5-14}$ aryl groups include phenyl, pyridyl, naphthyl, quinolinyl, anthracenyl and phenanthrenyl, which may be optionally substituted. In one embodiment, these groups are unsubstituted. In one embodiment, the $C_{5-14}$ aryl group is a $C_{6-14}$ carboaryl group. In one embodiment, the $C_{5-14}$ aryl group is a $C_{5-14}$ heteroaryl group. In one embodiment, Ar is phenyl, in particular unsubstituted phenyl. It has been found that the presence of a phenyl group provides polymers having a high refractive index.

In one embodiment, Ar is a $C_{5-14}$ aryl group optionally substituted with one or more groups selected from halogen, $C_{1-10}$ alkyl, $C_{3-10}$ cycloalkyl, $C_{5-36}$ aryl, $C_{6-38}$ arylalkyl, and $C_{1-7}$ alkoxy.

In one embodiment, the heteroatom X is sulphur. In one embodiment, X is oxygen.

Matsuda et al. (*Journal of Macromolecular Science*, Part A, Volume 36, Issue 9, 1999, pp. 1271-1288. "Novel Thiophene Methacrylates for Materials of High Refractive Index") report that thiophene methacrylate-based optical polymers have relatively high refractive index values and high ABBE values. This is indicative of a relatively small dispersion between the refractive index of red light ($n_C$) and the refractive index of blue light ($n_F$).

U.S. Pat. No. 3,799,972 describes polyacrylic resins containing thio-substituted polycyclic groups. The resins are reported as having high refractive index and high ABBE number. In contrast, resins containing aliphatic or alicyclic functionalities were said to have low refractive indexes and high ABBE values. Resins containing C,H-aromatic groups are said to have high refractive index and low chromatic dispersion values.

A material having a high refractive index and a high ABBE value may be used to prepare thin lenses with beneficial mechanical properties (eg. foldability). Such lenses may be prepared without compromising the optical properties of the material and chromatic aberrations (eg. flares, haloes) that can result from low chromatic dispersion values can be reduced or eliminated. The incorporation of high atomic refraction sulfur into the polymeric composition encourages this desirable blend of high refractive index and high ABBE value.

Generally, the sulphur atom in a thioether group is more chemically reactive than the oxygen atom in an analogous ether group. Thus, when the heteroatom X is sulphur, the chemical stability of the monomer is improved by the presence of the $R^2$ and $R^3$ substituents, which can shield the sulphur atom from physiochemical reactants.

The sterically-induced stabilisation provided by the $R^2$ and/or $R^3$ substituent(s) is particularly important for monomers having the structure given by general formula (III) when X is sulphur, where a methylene unit in the bridging group separates the sulphur atom from the aromatic (Ar) group.

For example, the monomer 2-(benzylthio)ethyl acrylate, which has no substituents adjacent to the sulphur heteroatom in the bridging group, is believed to degrade through oxidation by singlet oxygen. Fragmentation occurs concomitantly during oxidation at the benzylic carbon atom to form benzaldehyde, which can be extracted from the polymer. This degradation pathway results in the formation of extractable organic compounds (such as benzaldehyde) within an IOL implant. Polymers that can degrade to form an extractable organic compound are undesirable, particularly when the organic compound is an irritant (like benzaldehyde) because this impacts on bio-compatibility. The removal of the aromatic residue from the polymer side-chain will reduce the overall refractive index of the lens polymer, thereby lowering the focussing power of the intraocular lens.

The substituted methylene unit in the monomer of formula (III) prevents any appreciable bonding interaction between the p-orbitals of the oxygen or sulphur atom and the delocalised p-orbitals of the aromatic Ar group. When the oxygen or sulphur atom in an ether or thioether group is directly attached to an aryl group, the electrons in the non-bonding orbital of the heteroatom (the lone pair) may interact with the delocalised π-orbitals of the aromatic residue through a π-bonding interaction whereby electrons from the oxygen or sulfur atom are delocalised into the aromatic ring system.

This interaction between the oxygen or sulfur atom and the aromatic system raises the energy of the highest occupied molecular orbital (HOMO) and lowers that of the lowest unoccupied molecular orbital (LUMO) compared to an aromatic group with no substituents. Thus, in aryloxy or arylthio functional groups the HOMO-LUMO gap decreases relative to that of an unsubstituted aryl functional group and the resulting chromophore can absorb lower energy radiation. This decrease is most pronounced for arylthio functional groups.

Arylthio functional groups typically absorb UV-B radiation at 300 nm or above (due to π→π* electronic transitions). However, the cornea of the eye allows transmission of solar radiation having wavelengths greater than or equal to 300 nm. If the $Ar_\pi$—$O_p$ or $Ar_\pi$—$S_p$ interaction cannot take place, such as in the monomers represented by formula (III), then the Ar chromophore does not absorb as much UV-B radiation above 300 nm as an arylthio group. It is important for the long-term photostability of a lens under physiological conditions that it does not absorb significant quantity of UV-B radiation above 300 nm.

A second aspect of the invention is a polymerisable composition comprising one or more of the monomers defined in the first aspect of the invention. The present inventors have found that polymer ophthalmic lenses, particularly IOLs, formed from such a composition can be sufficiently flexible to fold or roll, so that IOLs are of a sufficiently small size for surgical insertion.

The amount of the above monomer or monomers in the polymerisable composition may be 5 to 99% by weight of the composition (preferably at least 20%), preferably 30 to 98% (preferably at least 50%) and more preferably at 70 to 95%. Monomers may be present in a polymerisable composition as a single structural isomer or as a mixture of two or more structural isomers. Alternatively the monomer may be present in a single enantiomeric form having a particular stereochemical configuration, as a mixture of enantiomers, or a mixture of structural isomers exhibiting more than one enantiomeric form.

The composition may further comprise one or more second monomers for forming a copolymer with the first monomer, the second monomers having at least one reactive unsaturated functionality, for example a vinyl, acrylate or methacrylate functionality.

The second monomers may be strengthening agents. Examples of suitable polymerisable strengthening agents are cyclohexyl methacrylate, cyclohexyl acrylate, cyclopentyl methacrylate, norbornyl methacrylate, isobornyl methacrylate, 2-methyl-adamantyl methacrylate, D,L-menthyl methacrylate, isophoryl methacrylate and styrene. A preferred strengthening agent for use in the present invention is methyl methacrylate. A strengthening agent may be incorporated into the polymerisable composition of the present invention at 0.5 to 25% by weight of the composition.

In one embodiment, the second monomers have an acrylate or methacrylate group. For example, the second monomers may be methyl acrylate, ethyl acrylate, propyl acrylate, butyl acrylate, hexyl acrylate, cyclohexyl acrylate, methoxymethyl acrylate, ethoxyethyl acrylate, methoxyethyl acrylate, ethoxymethyl acrylate, isobornyl acrylate, phenylether acrylate, methyl methacrylate, ethyl methacrylate, propyl methacrylate, butyl methacrylate, hexyl methacrylate, cyclohexyl methacrylate, methoxymethyl methacrylate, ethoxyethyl methacrylate, methoxyethyl methacrylate, ethoxymethyl methacrylate, isobornyl methacrylate and phenylether methacrylate.

In one embodiment, the amount of second monomer in the composition is 0.5 to 25% by weight of the composition.

In other embodiments, the amount of second monomer in the composition is at most 30% by weight of the composition, more preferably is at most 20%, and desirably at most 5%.

In one embodiment, the amount of second monomer in the composition is at least 0.1% by weight of the composition, at least 0.5% by weight of the composition, or at least 1% by weight of the composition.

The composition may further comprise one or more hydrophilic third monomers for forming a copolymer with the first monomer and optionally the second monomer. One or more hydrophilic monomers may be incorporated into the polymer to effect a down-modulation of the refractive index of the ultimate polymerised article and/or to control the mechanical properties of the polymers through the plasticising effect of water.

For example, the third monomers may be 2-hydroxyethyl methacrylate, 2-hydroxyethyl acrylate, 2-hydroxypropyl methacrylate, 2-hydroxypropyl acrylate, 2-N-vinyl pyrrolidinone, methacrylic acid, acrylic acid, acrylamide, methacrylamide, N,N-dimethyl acrylamide, N-methyl-N-vinylacetamide, 2-hydroxy-3-phenoxypropyl acrylate, glycerol monomethacrylate, polyethylene oxide monomethacrylate ($M_w$=200-400) and N-(2-hydroxypropyl)methacrylamide. A preferred hydrophilic monomer for use in the present invention is 2-hydroxyethyl methacrylate. In certain embodiments, the amount of the third monomers in the composition is 1 to 60% (preferably less than 50%) by weight of the composition, or less than 40% by weight, or less than 25% by weight or less than 15% by weight. In one embodiment, the amount of the third monomers in the composition is less than 5% by weight, or less than 2% by weight or less than 1% by weight.

The composition may further comprise one or more crosslinking fourth monomers having a minimum of two reactive, unsaturated functional groups, such as carbon-carbon double or triple bonds, so as to produce a three dimensional polymeric network. For example, the fourth monomers may be acrylate or methacrylate type compounds, such as ethylene glycol dimethylacrylate, ethyleneglycol diacrylate, diethylene glycol dimethylacrylate, diethylene glycol diacrylate, allyl acrylate, allyl methacrylate, 1,3-propanediol dimethacrylate, di-allyl maleate, 1,4-butanediol dimethacrylate and 1,4-butanediol diacrylate, 1,3-propanediol diacrylate, 1,3-propanediol dimethacrylate, 1,4-butanediol dimethacrylate, 1,6-hexanediol diacrylate, 1,6-hexanediol dimethacrylate, triethylene glycol diacrylate, triethylene glycol dimethacrylate, neopentyl glycol diacrylate, neopentyl glycol dimethacrylate, butylene glycol dimethacrylate, butylenes glycol diacrylate, thio-diethylene glycol diacrylate, thio-diethylene glycol dimethacrylate, trimethylolpropane triacrylate, and diacrylates and dimethacrylates of bisphenol A, bisphenol A ethoxylate (1-3EO/phenol), bisphenol A propoxylate (1-3EO/phenol). Other crosslinking fourth monomers include N,N'-dihydroxyethylene bisacrylamide, diallyl phthalate, triallyl cyanurate, divinylbenzene, ethylene glycol divinyl ether, N,N-methylene-bis-(meth)acrylamide, sulfonated divinylbenzene and divinylsulfone.

The cross-linking monomer may be used to modulate the material properties of the resulting polymer, most particularly the flexibility and elongation to break parameters. Preferably, the amount of the fourth monomer in the composition is at least 0.1% by weight of the composition, more preferably at least 0.5% and desirably at least 1%.

The optional addition of the second, third and/or fourth monomers to the composition can be useful for adjusting the physical or optical properties of the polymer formed from the composition.

For example, the monomers may be selected for the purpose of minimising the number and extent of glistenings in the polymer product. This may be achieved through the use of hydrophilic monomers, which may be cross-linking monomers, in the polymerisable composition. It is believed that the inclusion of a hydrophilic unit within the polymer encourages the even distribution of water throughout the polymer product, thereby minimising the accumulation of water in concentrated pockets.

The composition may further comprise conventional compounds, including but not limited to a thermally- or light-activated polymerisation initiator (preferably in an amount of up to 5% by weight of the composition), a UV-light absorber (preferably in an amount of up to 5% by weight of the composition), or a blue-light absorber (preferably in an amount of up to 0.5% by weight of the composition), or a combination thereof.

Examples of suitable UV-light blocking monomers or UV-light absorbers are substances containing a benzophenol or benzotriazol chromophore, such as 2-[3'-(2'H-benzotriazol-2'-yl)-4'-hydroxyphenyl]-ethylmethacrylate, 2-(4'-benzoyl-3'-hydroxyphenoxy)ethyl acrylate, 2-hydroxy-4-allyloxybenzophenone, 2-(2'-hydroxy-5-methacryloxyethylphenyl)-2H-benzotriazole, β-(4-benzotriazoyl-3-hydroxyphenoxy)ethylacrylate, 4-(2-acryloxyethoxy)-2-hydroxybenzophenone, 4-methacryloyloxy-2-hydroxybenzophenone, 2-(2'-methacryloyloxy-5'-methylphenyl)benzotriazole, 2-(2'-hydroxy-5'-methacryloxyethylphenyl)-2H-benzotriazole, 2-[3'-tert-butyl-2'-hydroxy-5'-(3"-methacryloyloxypropyl)phenyl]-5-chlorobenzotriazole, 2-(3'-tert-butyl-5'-(3"-dimethylvinylsilylpropoxy)-2'-hydroxyphenyl]-5-methoxybenzotriazole, 2-(3'-allyl-2'-hydroxy-5'-methylphenyl)benzotriazole, 2-[3'-tert-butyl-2'-hydroxy-5'-(3"-methacryloyloxypropoxy)phenyl]-5-methoxybenzotriazole, 2-[3'-tert-butyl-2'-hydroxy-5'-(3"-methacyloyloxypropoxy)phenyl]-5-chlorobenzotriazole, 2-(2'-hydroxy-5'-methacryloyloxyethylphenyl)-2H-benzotriazole and 2-(2'-hydroxy-3'-methallyl-5'-methylphenyl)benzotriazole. A preferred monomer as a UV-light absorber is 2-[3'-(2'H-benzotriazol-2'-yl)-4'-hydroxyphenyl]-ethylmethacrylate.

One or more tackiness modifying components may be added to the polymerisable composition according to the present invention. The inclusion of a tackiness modifying component can advantageously yield a more tractable polymer composition. Tackiness modifier agents typically contain at least one reactive unsaturated functionality, which is usually vinyl, acrylate or methacrylate based. Examples of tackiness modifying agents include fluorocarbon acrylates and methacrylates such as hexafluoro-iso-propyl methacrylate, 1H,1H,7H-dodecafluoroheptyl methacrylate, 1H,1H-heptafluorobutyl acrylate, 1H,1H,3H-hexafluorobutyl methacrylate, 1H,1H,5H-octafluoropentyl methacrylate, 2,2,2-trifluoroethyl acrylate, and linear-chain alkyl acrylates or methacrylates such as butyl acrylate, butyl methacrylate, pentyl acrylate, pentyl methacrylate, hexyl acrylate, hexyl methacrylate, heptyl acrylate, heptyl methacrylate, octyl acrylate, octyl methacrylate and/or branched-chain alkyl acrylates or methacrylates such as isopentyl acrylate, isopentyl methacrylate, isobutyl acrylate, isobutyl methacrylate, 2,2-dimethylpropyl acrylate, 2,2-dimethyl propyl methacrylate, 2-ethylhexyl acrylate and 2-ethylhexyl methacrylate.

A non-reactive diluent may be included in the polymerisable composition, which may be advantageous for the processing of the polymer after polymerisation, particularly during the expulsion of extractable contaminants, such as residual monomers, by treatment with an appropriate solvent. A pre-swelled polymer network of the polymer having an incorporated diluent facilitates the removal of residual, leachable contaminants from the body of the polymer. Solvent extraction of a dry polymer typically causes swelling of the polymer body which can lead to a degradation of the polymer mechanical properties. This effect may be mitigated by "pre-swelling" the polymer network with a diluent at an appropriate level.

Examples of suitable diluents include ethylene glycol, di(ethylene glycol), tetra(ethylene glycol), glycerol, 1,5-pentanediol, ethylene glycol monomethyl ether, ethylene glycol dimethyl ether, triethylene glycol monomethyl ether, 2-ethoxyethanol, solketal, benzonitrile, hexamethylphosphoramide, 2-N-methylpyrrolidinone and N,N-dimethylformamide. Preferred diluents for use in the present invention are 2-N-methylpyrrolidinone and N,N-dimethylformamide. The diluent is preferably included in the polymerisable composition at 2 to 40% by weight of the total polymerisable composition.

Polymerisable compositions according to the present invention can be polymerised by free-radical polymerisation, which may be initiated thermally or by ultraviolet light. The polymerisable composition may contain a free radical polymerisation initiator. Free radical polymerisation may be initiated thermally by using a thermal free radical initiator such as peroxide, peroxidedicarbonate or azo-based initiators. Examples of peroxide or peroxidedicarbonate based initiators are dilauroyl peroxide, didecanoyl peroxide, tert-butyl peroxyneodecanoate, di(4-tert-butylcyclohexyl) peroxydicarbonate, dicetyl peroxydicarbonate, dimyristyl peroxydicarbonate. Suitable examples of azo-based initiators include 1,1'-azobiscyanocyclohexane, 2,2'-azobis(2,4-dimethylvaleronitrile) and 2,2'-azobis(2-methylbutyronitrile). Photoinitiated free radical polymerisation can be carried out in the presence of a photoinitiator, such as CIBA's Irgacure® 1800 [comprising 25% bis(2,6-dimethoxybenzoyl)-2,4,4-trimethyl-pentylphosphineoxide and 75% 1-hydroxy-cyclohexyl-phenyl-ketone], Irgacure® 184 [comprising 100% 1-hydroxy-cyclohexyl-phenyl-ketone], Irgacure® 819 [comprising 100% bis(2,4,6-trimethylbenzoyl)-phenylphosphineoxide], Irgacure® 2959 [comprising 100% 1-[4-(2-hydroxyethoxy)-phenyl]-2-hydroxy-2-methyl-1-propane-1-one], Darocur® MBF [comprising 100% phenyl glyoxylic acid methyl ester], Darocur® TPO [comprising 100% 2,4,6-trimethylbenzoyl-diphenyl-phosphineoxide] and Darocur® 1173 [comprising 100% 2-hydroxy-2-methyl-1-phenyl-propan-1-one].

Thermally initiated free radical polymerisation is the preferred method of polymerising polymerisable compositions of the present invention. It is preferred that the polymerisable composition contains azobisisobutyronitrile (AIBN) as a free-radical initiator. Preferred quantities of the free-radical initiator are of 0.01 to 0.50% by weight of the polymerisable composition.

In one embodiment, the polymerisation is a bulk free radical polymerisation.

A third aspect of the present invention provides a polymer formed from the monomer of the first aspect of the invention or the polymerisable composition of the previous aspect. The polymers of the present invention are suitable for use in implantable medical devices, most particularly ophthalmic devices, such as IOLs. The polymers of the present invention contain one or more units having the formula (IV) or (IVa), which are formed from a monomer of the first aspect of the invention:

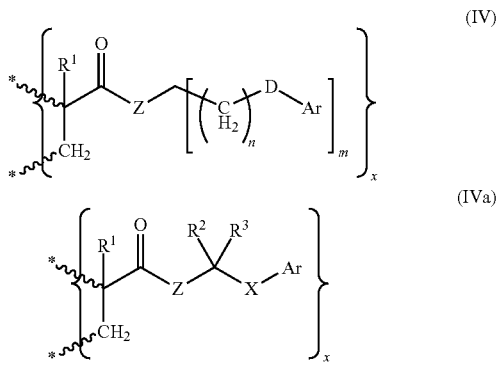

where $R^1$, Z, D, Ar, m and n are as defined for the compounds of formula (I) and (Ia). The preferences for $R^1$, Z, D, Ar, m and n for the compounds of formula (I), (Ia), (II) and (III) also apply to the units of formula (IV) and (IVa).

In one embodiment, the polymer contains one or more units of formula (IV).

In one embodiment, the amount of unit (IV) or (IVa) present in the polymer as a mole fraction of all the units present, is at least 0.40. In one embodiment, the mole fraction is at least 0.60, at least 0.80, at least 0.90, or at least 0.95. The final mole fraction of (IV) or (IVa) in the polymer may be altered by, for example, increasing or decreasing the amount of monomer of formula (I) or (Ia) in the polymerizable composition.

In one embodiment, the number average of units of (IV) and/or (IVa) present in the polymer is at least 100, or is at least 500, or is at least 1,000, or is at least 5,000.

In one embodiment, the average molecular weight of the polymer is at least 25,000 Da, or is at least 125,000 Da, or is least 250,000 Da, or is at least 1,250,000 Da.

A polymer according to the present invention is formed from monomers having an aromatic group, Ar, and an ether or thioether group, X. The polymer may also contain other components such as cross-linking monomers, hydrophilic monomers, UV-stabiliser monomers, polymerisable strengthening agents, polymerisable tack-modifiers and diluents. Examples of these other components are provided in the previous aspect of the invention.

An object of the invention is to prepare polymers that are optically transparent, have high refractive index, are soft, foldable, tack-free and biocompatible so that they may be used in the manufacture of implantable biomedical devices, such as ophthalmic intraocular lens implants, keratoprostheses, corneal rings or inlays, and contact lenses. The polymers produced according to the present invention should have sufficient flexibility for use as an implantable foldable intraocular lens device. Preferably, the polymers of the present invention are used to manufacture IOLs.

In one embodiment the polymer has a $T_g$ (as measured by dynamic mechanical thermal analysis, DMTA) in the range of −50 to 50° C., preferably −20 to 30° C. or more preferably in the range −15 to 25° C.

Preferably the polymer has an elongation at 20° C. of at least 50% (e.g., from 50% to 250%), and more preferably of at least 75% (e.g., from 75% to 150%). Most preferably the polymer has a $T_g$ less than 25° C. and an elongation to break of at least 100%.

The polymer is optically transparent and may have a refractive index (e.g., as measured by an Abbe refractometer) at 20° C. of at least 1.50.

In one embodiment, the polymer has a refractive index of at least 1.51, of at least 1.52, of at least 1.54, or of at least 1.55.

It is preferred that the polymer having a refractive index of at least 1.50 has an equilibrium water content in the range of 0 to 50 wt %. In one embodiment, the equilibrium water content is at most 20 wt %, or is at most 15 wt %, is at most 10 wt % or is at most 5 wt %.

In one aspect there is provided a polymer that is obtained or obtainable by a polymerisation reaction as described herein. In one embodiment, the polymer is obtained or obtainable from the polymerisation of a polymerizable composition as described herein.

Further aspects of the present invention provide a blank or cylindrical disc for an ophthalmic lens formed from the polymer of the previous aspect, and an ophthalmic lens (which is preferably an IOL) formed from a polymer of the previous aspect of the invention. The present invention includes methods for fabricating a blank for an ophthalmic lens and methods for fabricating an ophthalmic lens from a lens blank or from a polymer of a previous aspect of the invention.

Several methods can be used to manufacture or fabricate an ophthalmic lens according to the present invention. The lens can be prepared from a lens blank or cylindrical polymer disc using a cast moulding process. The blank or disc produced using these processes may then be machined using milling and lathe cutting processes familiar to those skilled in the art until a finished ophthalmic lens is obtained. Alternatively, a mould can be used to fabricate a completely or partly finished ophthalmic lens directly. Additional machining is required for a partly finished ophthalmic lens produced in this manner.

A first general method for fabricating an intraocular lens of the present invention involving the use of a blank for an ophthalmic lens. This method comprises the steps of:
(a) providing a blank according to a previous aspect of the invention; and
(b) machining the blank to form an ophthalmic lens.

Lens blanks or polymer discs according to the present invention may be manufactured according to one of the following methods. Reference to the shape or design of a mould as used herein refers to the shape or design of the part of the mould where the actual polymerisation of the polymer takes place.

A first method of providing or fabricating a lens blank or polymer disc is to mould a polymer of the present invention into a polymer rod. This method comprises the essential steps of:
(a) moulding a polymer of the present invention into a polymer rod using a rod-shaped mould,
(b) cutting or slicing the polymer rod into a series of discs or blanks.

A polymerisation reaction on the polymerisable composition of the present invention can be performed in the mould to form the polymer. Curing of the polymer thus obtained, or of an uncured polymer placed into the mould, may also be performed in the mould. An example of curing the polymer in the mould is described below in the button moulding method.

The rod-shaped (e.g. cylindrical) mould is typically constructed from polypolypropylene, polyethylene, PTFE or glass. The shape and size of the mould determines the diameter of the polymer rod. The diameter for the polymer rod is chosen for the design of the resulting ophthalmic lens to be formed; a larger diameter rod is required for a single piece ophthalmic lens and a smaller diameter rod is sufficient for a two or three-piece design ophthalmic lens. The polymer rod is then slit into a series of homogeneous discs with parallel faces.

A second method of providing or fabricating a lens blank or polymer disc is to mould a polymer of the present invention into a polymer disc using a button mould. This method comprises the step of moulding a polymer of the present invention into a polymer disc using a button mould.

A polymerisation reaction on the polymerisable composition of the present invention can be performed in the mould to form the polymer. Curing of the polymer thus obtained, or of an uncured polymer placed into the mould, may also be performed in the mould.

Typically, button moulds consist of an array of button impressions on a pre-formed polypropylene, polyethylene or PTFE sheet. The diameter of the individual button moulds is determined by the resulting design of the final lens. Button moulds with a larger diameter button are required for a single piece ophthalmic lens, and a smaller diameter button mould is sufficient for a two or three-piece design ophthalmic lens.

The mould-sheet is covered with a lid-stock, typically comprising polyethylene or polypropylene. The lid-stock covered mould-sheet is filled with the polymer composition of the present invention and the mould is sealed, typically using a heating sealing bar apparatus. A polymerisable composition can be prepared or a polymer can be thermally cured in the mould using an oven or, more preferentially, in a water bath thermally equilibrated to the required temperature. The water bath is typically degassed to remove dissolved oxygen that might inhibit the free-radical polymerisation process.

Once polymerisation and/or curing is complete, the water bath is allowed to cool and the mould-sheet is removed, cleaned and dried. The lid-stock can then be peeled from the mould and the polymerised discs extruded. It may be advantageous to perform the lid-stock removal and mould extrusion at a depressed temperature to prevent possible damage to the relatively soft polymer disc. This is particularly important when diluents are employed in the polymerisable composition. In such instances the mould may be chilled to a temperature lower than that of the freezing point of the diluent or, where a diluent is not employed, the $T_g$ of the polymer for a period of 5 to 60 minutes immediately prior to lid-stock removal and subsequent mould extrusion.

Both of the above moulding methods for providing a lens blank or polymer disc may include an additional step of purging the polymer rod or disc initially formed after the polymerisation and/or curing step. The purging step comprises treating the polymer rod or disc with an appropriate solvent to remove extractable contaminants. An example of a suitable solvent for extracting contaminants is acetonitrile.

It may also be desirable to include a drying step after the polymerisation and/or curing step, and after any purging step. The polymer rod or disc may be dried or annealed at an elevated temperature, either in air, an inert atmosphere of nitrogen or argon or under reduced pressure (in vacuo). Preferably, the drying or annealing step is performed under reduced pressure (in vacuo). The drying step may be carried out at a temperature of 30 to 150° C. The drying step may be performed at reduced pressure, for example at a pressure of 0.001 to 300 torr, or preferably 0.01 to 10 torr, or most preferably 0.03 to 0.30 torr.

A polymer disc or lens blank obtained using the above moulding methods may be ground and polished. The above moulding methods may include a grinding and polishing step so that the disc or blank achieves a high degree of tolerance for the accuracy of both the diameter of the disc and the parallel faces.

In the first general method of fabricating an ophthalmic lens, the lens blank or polymer disc is lathe cut and machine milled into the required lens shape. The step of machining a blank or polymer disc to form an ophthalmic lens comprises the following steps:
(a) lathe machining a first surface of an ophthalmic lens from a polymer disc,
(b) lathe machining a second surface of an ophthalmic lens from said polymer disc.

Before each lathe machining step, the polymer disc is adhered or blocked onto a chuck (typically a brass-chuck) or poly methylmethacrylate cylinder. This may be achieved by using a low temperature blocking wax. Depending on the cutting parameters employed, it may be desirable to cool the disc during lathing, such as with a cool-air stream, such as that provided by a vortex cold-air tube or a cryogenic air-stream. Additional benefit may also be gained through the use of a cryogenic lathing system where the actual polymer blank and the cutting tool are held at low temperatures during the cutting process.

After each ophthalmic lens surface has been lathe machined into the polymer, the machined surface may be inspected for defects. Haptics may then be milled or fitted, depending on the ophthalmic lens design. Typically, the final ophthalmic lens is then inspected for defects.

For example, a typical method of lathe machining an IOL from a blank or a polymer disc is as follows:
(i) Block the polymer disc on a chuck or a poly methyl methacrylate cylinder using a low temperature blocking wax.
(ii) Apply a cold-air stream onto the rotating disc, such as by using a vortex cold-air tube, and lathe machine the first surface of a lens from a polymer disc.

(iii) Inspect the machined surface for defects. If no defects are present, then de-block the machined polymer disc.
(iv) Block the first surface of the polymer disc onto the chuck using a low temperature blocking wax.
(v) Apply a cold-air stream onto the rotating disc, for example, by using a vortex cold-air tube. Then lathe the second surface of the lens optic from the polymer disc,
(vi) Inspect the machined surface for defects.
(vii) For a one piece IOL design, mill the haptics. A cold-air stream may optionally be applied. For a multi-piece IOL design, attach the IOL haptics.
(viii) De-block the IOL, for example by dissolving the blocking wax with 80-100 petroleum ether.
(ix) Hydrate the IOL in physiological saline.
(x) Polish the IOL to smooth the lens surfaces and the lens edges.
(xi) Inspect the final IOL for defects.

A second general method of fabricating an ophthalmic lens (preferably an IOL) of the present invention involves the formation of a partial or complete lens using a mould designed specifically for that purpose. This method comprises the essential step of:

moulding a polymer according to the present invention to form the anterior and/or
posterior portion of an opthalmic lens directly.

The polymerisable composition of the present invention may be polymerised in the mould to form the polymer. Curing of the polymer thus obtained, or of an uncured polymer placed into the mould, may also be carried out in the mould. The mould design may encompass the anterior or posterior portion of the lens, or the complete lens. If only one lens surface is directly moulded, then the optics of the complementary surface must be lathed and machine milled at room temperature or at a depressed temperature, as described above. The mould design can encompass a single piece IOL design that incorporates moulded haptics or, alternatively, the haptics can be machined subsequent to the polymerisation. Another alternative is a mould design that can produce a finished or semi-finished lens to which the haptics are subsequently attached to yield a two or three-piece IOL design. Purging and/or drying steps, as described above, may be included in the moulding method of a partial or complete lens.

In the method of moulding partially finished lens shapes, a machining step is necessary to produce the complete finished lens. The lathing and machining to be carried out depends on what facets of the optic or haptics remain to be completed. For example, for a semi-finished lens shape with a completed first surface, then the above lathe-machining protocol should followed from instructions (iv) to (ix). The steps generally described above for the lathe machining method can be used to machine a second complete surface and/or to mill or attach haptics to an ophthalmic lens that is moulded as a partially finished lens shape.

DEFINITIONS

Substituents are defined and exemplified below.

$C_{1-10}$ alkyl: The term "$C_{1-10}$ alkyl" as used herein, pertains to a monovalent moiety obtained by removing a hydrogen atom from a carbon atom of a hydrocarbon compound having from 1 to 10 carbon atoms.

Examples of saturated alkyl groups include, but are not limited to, methyl ($C_1$), ethyl ($C_2$), propyl ($C_3$), butyl ($C_4$), pentyl ($C_5$), hexyl ($C_6$), heptyl ($C_7$) etc.

Examples of saturated linear alkyl groups include, but are not limited to, methyl ($C_1$), ethyl ($C_2$), n-propyl ($C_3$), n-butyl ($C_4$), n-pentyl (amyl) ($C_5$), n-hexyl ($C_6$) and n-heptyl ($C_7$).

Examples of saturated branched alkyl groups include iso-propyl ($C_3$), iso-butyl ($C_4$), sec-butyl ($C_4$), tert-butyl ($C_4$), iso-pentyl ($C_5$), and neo-pentyl ($C_5$).

$C_{3-10}$ cycloalkyl: The term "$C_{3-10}$ cycloalkyl" as used herein, pertains to an alkyl group which is also a cyclyl group; that is, a monovalent moiety obtained by removing a hydrogen atom from an alicyclic ring atom of a cyclic hydrocarbon (carbocyclic) compound, which moiety has from 3 to 10 carbon atoms, including from 3 to 10 ring atoms.

Examples of cycloalkyl groups include, but are not limited to, those derived from:

saturated monocyclic hydrocarbon compounds:
cyclopropane ($C_3$), cyclobutane ($C_4$), cyclopentane ($C_5$), cyclohexane ($C_6$), cycloheptane ($C_7$), methylcyclopropane ($C_4$), dimethylcyclopropane ($C_5$), methylcyclobutane ($C_5$), dimethylcyclobutane ($C_6$), methylcyclopentane ($C_6$), dimethylcyclopentane ($C_7$) and methylcyclohexane ($C_7$); and saturated polycyclic hydrocarbon compounds:
norcarane ($C_7$), norpinane ($C_7$), norbornane ($C_7$).

$C_{2-11}$ alkyl ether: The term "$C_{2-11}$ alkyl ether" as used herein, pertains to a monovalent moiety obtained by removing a hydrogen atom from a carbon atom of a dialkylether compound (a compound of the form R—O—R', where R and R' are alkyl groups as defined above) having from 2 to 11 carbon atoms. Each alkyl group in the parent dialkylether compound may independently be linear or branched.

Examples of alkyl ether groups only containing linear alkyl groups include, but are not limited to, methoxymethyl ($CH_3OCH_2$—) ($C_2$), ethoxymethyl ($CH_3CH_2OCH_2$—) ($C_3$), methoxyethyl ($CH_3OCH_2OH_2$—) ($C_3$), ethoxyethyl ($CH_3CH_2OCH_2CH_2$—) ($C_4$), propoxymethyl ($CH_3CH_2CH_2OCH_2$—) ($C_4$), methoxypropyl ($CH_3OCH_2CH_2CH_2$—) ($C_4$), etc.

Examples of alkyl ether groups containing a branched alkyl group include, but are not limited to, 1-(methoxy)ethyl ($CH_3OCH(CH_3)$—) ($C_3$), 1-(methoxy)propyl ($CH_3OCH(CH_2CH_3)$—) ($C_4$), 2-(methoxy)propyl ($CH_3OCH(CH_3)CH_2$—) ($C_4$), i-propyloxymethyl (($CH_3)_2CHOCH_2$—), 1-(i-propyloxy)ethyl ((($CH_3)_2CHOCH(CH_3)$—) ($C_5$), etc.

$C_{2-11}$ alkyl thioether: The term "$C_{2-11}$ alkyl thioether" as used herein, pertains to a monovalent moiety obtained by removing a hydrogen atom from a carbon atom of a dialkylthioether compound (a compound of the form R—S—R', where R and R' are alkyl groups as defined above) having from 2 to 11 carbon atoms. Each alkyl group in the parent dialkylthioether compound may independently be linear or branched.

The definition of an alkyl thioether is analogous to the definition of an alkyl ether given above, except that the oxygen atom in the alkyl ether group is substituted for a sulphur atom.

$C_{4-36}$ heterocyclyl: The term "$C_{4-36}$ heterocyclyl" as used herein, pertains to a monovalent moiety obtained by removing a hydrogen atom from a ring atom of a heterocyclic compound, which moiety has from 4 to 36 ring atoms, of which from 1 to 10 are ring heteroatoms. Preferably, each ring has from 3 to 7 ring atoms, of which from 1 to 4 are ring heteroatoms.

In this context, the prefixes (e.g. $C_{3-20}$, $C_{3-7}$, $C_{5-6}$, etc.) denote the number of ring atoms, or range of number of ring atoms, whether carbon atoms or heteroatoms. For example, the term "$C_{5-6}$ heterocyclyl", as used herein, pertains to a heterocyclyl group having 5 or 6 ring atoms.

Examples of monocyclic heterocyclyl groups include, but are not limited to, those derived from:

$N_1$: azetidine ($C_4$), pyrrolidine (tetrahydropyrrole) ($C_5$), pyrroline (e.g., 3-pyrroline, 2,5-dihydropyrrole) ($C_5$), 2H-pyrrole or 3H-pyrrole (isopyrrole, isoazole) ($C_5$), piperidine ($C_6$), dihydropyridine ($C_6$), tetrahydropyridine ($C_6$), azepine ($C_7$);

$O_1$: oxetane ($C_4$), oxolane (tetrahydrofuran) ($C_5$), oxole (dihydrofuran) ($C_5$), oxane (tetrahydropyran) ($C_6$), dihydropyran ($C_6$), pyran ($C_6$), oxepin ($C_7$);

$S_1$: thietane ($C_4$), thiolane (tetrahydrothiophene) ($C_5$), thiane (tetrahydrothiopyran) ($C_6$), thiepane ($C_7$);

$O_2$: dioxolane ($C_5$), dioxane ($C_6$), and dioxepane ($C_7$);

$O_3$: trioxane ($C_6$);

$N_2$: imidazolidine ($C_5$), pyrazolidine (diazolidine) ($C_5$), imidazoline ($C_5$), pyrazoline (dihydropyrazole) ($C_5$), piperazine ($C_6$);

$N_1O_1$: tetrahydrooxazole ($C_5$), dihydrooxazole ($C_5$), tetrahydroisoxazole ($C_5$), dihydroisoxazole ($C_5$), morpholine ($C_6$), tetrahydrooxazine ($C_6$), dihydrooxazine ($C_6$), oxazine ($C_6$);

$N_1S_1$: thiazoline ($C_5$), thiazolidine ($C_5$), thiomorpholine ($C_6$);

$N_2O_1$: oxadiazine ($C_6$);

$O_1S_1$: oxathiole ($C_5$) and oxathiane (thioxane) ($C_6$); and, $N_1O_1S_1$: oxathiazine ($C_6$).

Examples of substituted monocyclic heterocyclyl groups include those derived from saccharides, in cyclic form, for example, furanoses ($C_5$), such as arabinofuranose, lyxofuranose, ribofuranose, and xylofuranse, and pyranoses ($C_6$), such as allopyranose, altropyranose, glucopyranose, mannopyranose, gulopyranose, idopyranose, galactopyranose, and talopyranose.

$C_{5-36}$ aryl: The term "$C_{5-36}$ aryl", as used herein, pertains to a monovalent moiety obtained by removing a hydrogen atom from an aromatic ring atom of an aromatic compound, which moiety has from 6 to 36 ring atoms. Preferably, each ring has from 5 to 10 ring atoms.

In this context, the prefixes (e.g. $C_{3-20}$, $C_{5-7}$, $C_{5-6}$, etc.) denote the number of ring atoms, or range of number of ring atoms, whether carbon atoms or heteroatoms. For example, the term "$C_{5-6}$ aryl" as used herein, pertains to an aryl group having 5 or 6 ring atoms.

The ring atoms may be all carbon atoms, as in "carboaryl groups". Examples of carboaryl groups include, but are not limited to, those derived from benzene (i.e. phenyl) ($C_6$), naphthalene ($C_{10}$), azulene ($C_{10}$), anthracene ($C_{14}$), phenanthrene ($C_{14}$), naphthacene ($C_{16}$), and pyrene ($C_{16}$).

Examples of aryl groups which comprise fused rings, at least one of which is an aromatic ring, include, but are not limited to, groups derived from indane (e.g. 2,3-dihydro-1H-indene) ($C_9$), indene ($C_9$), isoindene ($C_9$), tetraline (1,2,3,4-tetrahydronaphthalene ($C_{10}$), acenaphthene ($C_{12}$), fluorene ($C_{13}$), phenalene ($C_{13}$), acephenanthrene ($C_{15}$), and aceanthrene ($C_{16}$).

Alternatively, the ring atoms may include one or more heteroatoms, as in "heteroaryl groups". Examples of monocyclic heteroaryl groups include, but are not limited to, those derived from:

$N_1$: pyrrole (azole) ($C_5$), pyridine (azine) ($C_6$);

$O_1$: furan (oxole) ($C_5$);

$S_1$: thiophene (thiole) ($C_5$);

$N_1O_1$: oxazole ($C_5$), isoxazole ($C_5$), isoxazine ($C_6$);

$N_2O_1$: oxadiazole (furazan) ($C_5$);

$N_3O_1$: oxatriazole ($C_s$);

$N_1S_1$: thiazole ($C_5$), isothiazole ($C_6$);

$N_2$: imidazole (1,3-diazole) ($C_5$), pyrazole (1,2-diazole) ($C_5$), pyridazine (1,2-diazine) ($C_6$), pyrimidine (1,3-diazine) ($C_6$) (e.g., cytosine, thymine, uracil), pyrazine (1,4-diazine) ($C_6$);

$N_3$: triazole ($C_5$), triazine ($C_6$); and, $N_4$: tetrazole ($C_5$).

Examples of heteroaryl which comprise fused rings, include, but are not limited to:

$C_9$ (with 2 fused rings) derived from benzofuran ($O_1$), isobenzofuran ($O_1$), indole ($N_1$), isoindole ($N_1$), indolizine ($N_1$), indoline ($N_1$), isoindoline ($N_1$), purine ($N_4$) (e.g., adenine, guanine), benzimidazole ($N_2$), indazole ($N_2$), benzoxazole ($N_1O_1$), benzisoxazole ($N_1O_1$), benzodioxole ($O_2$), benzofurazan ($N_2O_1$), benzotriazole ($N_3$), benzothiofuran ($S_1$), benzothiazole benzothiadiazole ($N_2S$);

$C_{10}$ (with 2 fused rings) derived from chromene ($C_1$), isochromene ($C_1$), chroman ($O_1$), isochroman ($C_1$), benzodioxan ($O_2$), quinoline ($N_1$), isoquinoline ($N_1$), quinolizine ($N_1$), benzoxazine ($N_1O_1$), benzodiazine ($N_2$), pyridopyridine ($N_2$), quinoxaline ($N_2$), quinazoline (N2), cinnoline ($N_2$), phthalazine ($N_2$), naphthyridine ($N_2$), pteridine ($N_4$);

$C_{11}$ (with 2 fused rings) derived from benzodiazepine ($N_2$);

$C_{13}$ (with 3 fused rings) derived from carbazole ($N_1$), dibenzofuran ($O_1$), dibenzothiophene ($S_1$), carboline ($N_2$), perimidine ($N_2$), pyridoindole ($N_2$); and, $C_{14}$ (with 3 fused rings) derived from acridine ($N_1$), xanthene ($C_1$), thioxanthene ($S_1$), oxanthrene ($O_2$), phenoxathiin ($O_1S_1$), phenazine ($N_2$), phenoxazine ($N_1O_1$), phenothiazine ($N_1S_1$), thianthrene ($S_2$), phenanthridine ($N_1$), phenanthroline ($N_2$), phenazine ($N_2$).

$C_{6-37}$ aryl ether: The term "$C_{6-37}$ aryl ether" as used herein, pertains to a monovalent moiety obtained by removing a hydrogen atom from the carbon atom of the alkyl group in an aryl-alkyl-ether compound having from 6 to 37 carbon atoms, i.e. compounds of the form R—O—Z, where R is an alkyl group and Z is an aryl group, both alkyl and aryl groups are as defined above. The alkyl group in the parent aryl-alkyl-ether compound may be linear or branched.

The term "$C_{6-37}$ aryl ether" as used herein, also pertains to a monovalent moiety obtained by removing a hydrogen atom from the carbon atom of the alkyl group in an aryl-alkyl-ether compound having from 6 to 37 carbon atoms where the aryl group is attached to the oxygen atom of the alkyl-ether (alkoxy) unit by a methylene group, i.e. compounds of the form R—O—$CH_2$—Z, where R is an alkyl group and Z is an aryl group, both alkyl and aryl groups are as defined above. The methylene group connecting the aryl group (Z) to the oxygen atom of the ether unit may be substituted by an alkyl group, as defined above.

Examples of aryl ether groups include, but are not limited to, the following carboaryl ethers: phenoxymethyl (PhOCH—) ($C_7$), 2-phenoxyethyl (PhOCH$_2$CH$_2$—) ($C_8$), 1-phenoxyethyl (PhOCH(CH$_3$)—) ($C_8$), benzyloxymethyl (PhCH$_2$OCH$_2$—) ($C_8$), (1-phenyl,-1-ethyl)oxymethyl (PhCH(CH$_3$)OCH$_2$—) ($C_9$) etc.

$C_{6-37}$ aryl thioether: The term "$C_{6-37}$ aryl thioether" as used herein, pertains to a monovalent moiety obtained by removing a hydrogen atom from the carbon atom of the alkyl group in an aryl-alkyl-thioether compound having from 6 to 37 carbon atoms, i.e. compounds of the form R—S—Z, where R is an alkyl group and Z is an aryl group, both alkyl and aryl groups are as defined above. The alkyl group in the parent aryl-alkyl-thioether compound may be linear or branched.

The term "$C_{6-37}$ aryl thioether" as used herein, also pertains to a monovalent moiety obtained by removing a hydrogen atom from the carbon atom of the alkyl group in an aryl-alkyl-thioether compound having from 6 to 37 carbon atoms where the aryl group is attached to the sulphur atom of the alkyl-thioether unit by a methylene group, i.e. compounds of the form R—S—$CH_2$—Z, where R is an alkyl group and Z is an aryl group, both alkyl and aryl groups are as defined above.

The methylene group connecting the aryl group (Z) to the sulphur atom of the ether unit may be substituted by an alkyl group, as defined above.

The definition of an alkyl thioether is analogous to the definition of an aryl ether given above, except that the oxygen atom in the alkyl ether group is substituted for a sulphur atom.

Examples of aryl thioether groups include, but are not limited to the following carboaryl thioethers: PhSCH$_2$— (C$_7$), PhSCH$_2$CH$_2$— (C$_8$), PhSCH(CH$_3$)— (C$_8$), PhCH$_2$SCH$_2$— (C$_8$), PhCH(CH$_3$)SCH$_2$— (C$_9$) etc.

C$_{6-36}$ aryloxy: The term "C$_{5-36}$ aryloxy", as used herein, pertains to a monovalent moiety obtained by removing a hydrogen atom from the oxygen atom of alcohol group (OH) attached to an aromatic compound. The aryl part of the aromatic compound is as defined above. The term "C$_{5-36}$ aryloxy" as used herein, also pertains to a monovalent moiety obtained by removing a hydrogen atom from the oxygen atom of alcohol group (OH) attached to an aromatic compound where the aryl group is attached to the oxygen atom of the alcohol (hydroxy) unit by a methylene group, i.e. compounds of the form H—O—CH$_2$—Z, where Z is an aryl group as defined above. The methylene group connecting the aryl group (Z) to the oxygen atom of the alcohol unit may be substituted by an alkyl group, as defined above. The aromatic compound has from 5 to 36 ring atoms. Preferably, each ring has from 5 to 10 ring atoms.

In this context, the prefixes (e.g. C$_{3-20}$, C$_{5-7}$, C$_{5-6}$, etc.) denote the number of ring atoms or range of number of ring atoms, whether carbon atoms or heteroatoms, and the total number of carbon atoms in any methylene group (and alkyl groups attached to the methylene group) that connects the aryl group to the alcohol oxygen atom. For example, the term "C$_{6-7}$ aryloxy" as used herein, pertains to an aryloxy group having 6 or 7 ring atoms, or to an aryl-CH$_2$—O where the aryl group has 6 ring atoms.

Examples of aryloxy groups include, but are not limited to, phenoxy (PhO—) (C$_6$), benzyloxy (PhCH$_2$O—) (C$_7$), (1-phenyl,-1-ethyl)oxy (PhCH(CH$_3$)O—) (C$_8$) etc.

C$_{6-38}$ arylalkyl: The term "C$_{6-38}$ arylalkyl", as used herein, pertains to a monovalent moiety obtained by removing a hydrogen atom from a carbon atom of alkyl group that is covalently bonded to an aromatic ring. The aryl part of the aromatic compound is as defined above. The aromatic compound has from 5 to 36 ring atoms. Preferably, each ring has from 5 to 10 ring atoms.

The prefixes (e.g. C$_{3-20}$, C$_{5-7}$, C$_{5-6}$, etc.) denote the number of carbon atoms in the alkyl group and the total number of ring atoms. For example, the term "C$_8$ arylalkyl" as used herein, pertains to an arylalkyl group where the aryl group has 6 or 7 ring atoms and the alkyl chain has 1 or 2 carbon atoms. An example of a C$_7$ arylalkyl group is a benzyl group (PhCH$_2$—).

C$_{5-38}$ heterocyclyl-alkyl: The term "C$_{5-38}$ heterocyclyl-alkyl", as used herein, pertains to a monovalent moiety obtained by removing a hydrogen atom from a carbon atom of alkyl group that is covalently bonded to a heterocyclic compound. The heterocyclic ring or heterocyclyl group is as defined above and has from 4 to 36 ring atoms, of which from 1 to 10 are ring heteroatoms. Preferably, each ring has from 3 to 7 ring atoms, of which from 1 to 4 are ring heteroatoms.

In this context, the prefixes (e.g. C$_{3-20}$, C$_{3-7}$, C$_{5-6}$, etc.) denote the number of carbon atoms in the alkyl group and the total number of ring atoms, whether carbon atoms or heteroatoms. For example, the term "C$_{6-7}$ heterocyclyl", as used herein, pertains to a heterocyclyl group having 5 or 6 ring atoms and an alkyl group having 1 or 2 carbon atoms.

Halogen atom: The term used herein refers to —F, —Cl, —Br and —I substituents.

The phrase "optionally substituted" as used herein, pertains to a parent group which may be unsubstituted or which may be substituted.

Unless otherwise specified, the term "substituted" as used herein, pertains to a parent group which bears one or more substituents. The term "substituent" is used herein in the conventional sense and refers to a chemical moiety which is covalently attached to, or if appropriate, fused to, a parent group. A wide variety of substituents are well known, and methods for their formation and introduction into a variety of parent groups are also well known. If a group is optionally substituted and the optional substituent(s) are not listed, then the optional substituent(s) may be selected from one or more of the groups listed above or groups listed below.

Hydroxy: —OH.

Ether: —OR, wherein R is an ether substituent, for example, a C$_{1-7}$ alkyl group (also referred to as a C$_{1-7}$ alkoxy group, discussed below), a C$_{3-20}$ heterocyclyl group (also referred to as a C$_{3-20}$ heterocyclyloxy group), or a C$_{5-20}$ aryl group (also referred to as a C$_{5-20}$ aryloxy group), preferably a C$_{1-7}$ alkyl group.

Alkoxy: —OR, wherein R is an alkyl group, for example, a C$_{1-7}$ alkyl group. Examples of C$_{1-7}$ alkoxy groups include, but are not limited to, —OMe (methoxy), —OEt (ethoxy), —O(nPr) (n-propoxy), —O(iPr) (isopropoxy), —O(nBu) (n-butoxy), —O(sBu) (sec-butoxy), —O(iBu) (isobutoxy), and —O(tBu) (tert-butoxy).

Acetal: —CH(OR$^1$)(OR$^2$), wherein R$^1$ and R$^2$ are independently acetal substituents, for example, a C$_{1-7}$ alkyl group, a C$_{3-20}$ heterocyclyl group, or a C$_{8-20}$ aryl group, preferably a C$_{1-7}$ alkyl group, or, in the case of a "cyclic" acetal group, R$^1$ and R$^2$, taken together with the two oxygen atoms to which they are attached, and the carbon atoms to which they are attached, form a heterocyclic ring having from 4 to 8 ring atoms. Examples of acetal groups include, but are not limited to, —CH(OMe)$_2$, —CH(OEt)$_2$, and —CH(OMe)(OEt).

Hemiacetal: —CH(OH)(OR$^1$), wherein R$^1$ is a hemiacetal substituent, for example, a C$_{1-7}$ alkyl group, a C$_{3-20}$ heterocyclyl group, or a C$_{5-20}$ aryl group, preferably a C$_{1-7}$ alkyl group. Examples of hemiacetal groups include, but are not limited to, —CH(OH)(OMe) and —CH(OH)(OEt).

Ketal: —CR(OR$^1$)(OR$^2$), where R$^1$ and R$^2$ are as defined for acetals, and R is a ketal substituent other than hydrogen, for example, a C$_{1-7}$ alkyl group, a C$_{3-20}$ heterocyclyl group, or a C$_{5-20}$ aryl group, preferably a C$_{1-7}$ alkyl group. Examples ketal groups include, but are not limited to, —C(Me)(OMe)$_2$, —C(Me)(OEt)$_2$, —C(Me)(OMe)(OEt), —C(Et)(OMe)$_2$, —C(Et)(OEt)$_2$, and —C(Et)(OMe)(OEt).

Hemiketal: —CR(OH)(OR$^1$), where R$^1$ is as defined for hemiacetals, and R is a hemiketal substituent other than hydrogen, for example, a C$_{1-7}$ alkyl group, a C$_{3-20}$ heterocyclyl group, or a C$_{5-20}$ aryl group, preferably a C$_{1-7}$ alkyl group. Examples of hemiacetal groups include, but are not limited to, —C(Me)(OH)(OMe), —C(Et)(OH)(OMe), —C(Me)(OH)(OEt), and —C(Et)(OH)(OEt).

Oxo (keto, -one): =O.

Thione (thioketone): =S.

Imino (imine): =NR, wherein R is an imino substituent, for example, hydrogen, C$_{1-7}$ alkyl group, a C$_{3-20}$ heterocyclyl group, or a C$_{5-20}$ aryl group, preferably hydrogen or a C$_{1-7}$ alkyl group. Examples of ester groups include, but are not limited to, =NH, =NMe, =NEt, and =NPh.

Acyl (keto): —C(=O)R, wherein R is an acyl substituent, for example, a C$_{1-7}$ alkyl group (also referred to as C$_{1-7}$ alkylacyl or C$_{1-7}$ alkanoyl), a C$_{3-20}$ heterocyclyl group (also referred to as C$_{3-20}$ heterocyclylacyl), or a C$_{5-20}$ aryl group (also referred to as C$_{5-20}$ arylacyl), preferably a C$_{1-7}$ alkyl group. Examples of acyl groups include, but are not limited to, —C(=O)CH₃ (acetyl), —C(=O)CH₂CH₃ (propionyl), —C(=O)C(CH₃)₃ (t-butyryl), and —C(=O)Ph (benzoyl, phenone).

Ester (carboxylate, carboxylic acid ester, oxycarbonyl): —C(=O)OR, wherein R is an ester substituent, for example, a $C_{1-7}$ alkyl group, a $C_{3-20}$ heterocyclyl group, or a $C_{5-20}$ aryl group, preferably a $C_{1-7}$ alkyl group. Examples of ester groups include, but are not limited to, —C(=O)OCH₃, —C(=O)OCH₂CH₃, —C(=O)OC(CH₃)₃, and —C(=O)OPh.

Acyloxy (reverse ester): —OC(=O)R, wherein R is an acyloxy substituent, for example, a $C_{1-7}$ alkyl group, a $C_{3-20}$ heterocyclyl group, or a $C_{5-20}$ aryl group, preferably a $C_{1-7}$ alkyl group. Examples of acyloxy groups include, but are not limited to, —OC(=O)CH₃ (acetoxy), —OC(=O)CH₂CH₃, —OC(=O)C(CH₃)₃, —OC(=O)Ph, and —OC(=O)CH₂Ph.

Oxycarboyloxy: —OC(=O)OR, wherein R is an ester substituent, for example, a $C_{1-7}$ alkyl group, a $C_{3-20}$ heterocyclyl group, or a $C_{5-20}$ aryl group, preferably a $C_{1-7}$ alkyl group. Examples of ester groups include, but are not limited to, —OC(=O)OCH₃, —OC(=O)OCH₂CH₃, —OC(=O)OC(CH₃)₃, and —OC(=O)OPh.

Amido (carbamoyl, carbamyl, aminocarbonyl, carboxamide): —C(=O)NR¹R², wherein R¹ and R² are independently amino substituents, as defined for amino groups. Examples of amido groups include, but are not limited to, —C(=O)NH₂, —C(=O)NHCH₃, —C(=O)N(CH₃)₂, —C(=O)NHCH₂CH₃, and —C(=O)N(CH₂CH₃)₂, as well as amido groups in which R¹ and R², together with the nitrogen atom to which they are attached, form a heterocyclic structure as in, for example, piperidinocarbonyl, morpholinocarbonyl, thiomorpholinocarbonyl, and piperazinocarbonyl.

Acylamido (acylamino): —NR¹C(=O)R², wherein R¹ is an amide substituent, for example, hydrogen, a $C_{1-7}$ alkyl group, a $C_{3-20}$ heterocyclyl group, or a $C_{5-20}$ aryl group, preferably hydrogen or a $C_{1-7}$ alkyl group, and R² is an acyl substituent, for example, a $C_{1-7}$ alkyl group, a $C_{3-20}$ heterocyclyl group, or a $C_{5-20}$ aryl group, preferably hydrogen or a $C_{1-7}$ alkyl group. Examples of acylamide groups include, but are not limited to, —NHC(=O)CH₃, —NHC(=O)CH₂CH₃, and —NHC(=O)Ph. R¹ and R² may together form a cyclic structure, as in, for example, succinimidyl, maleimidyl, and phthalimidyl:

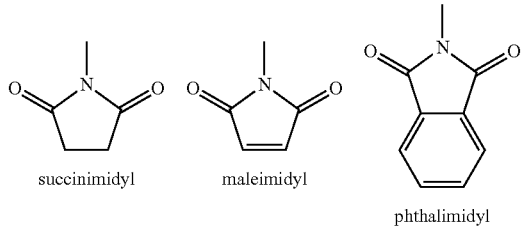

succinimidyl    maleimidyl    phthalimidyl

Aminocarbonyloxy: —OC(=O)NR¹R², wherein R¹ and R² are independently amino substituents, as defined for amino groups. Examples of aminocarbonyloxy groups include, but are not limited to, —OC(=O)NH₂, —OC(=O)NHMe, —OC(=O)NMe₂, and —OC(=O)NEt₂.

Imino: =NR, wherein R is an imino substituent, for example, for example, hydrogen, a $C_{1-7}$ alkyl group, a $C_{3-20}$ heterocyclyl group, or a $C_{5-20}$ aryl group, preferably H or a $C_{1-7}$ alkyl group. Examples of imino groups include, but are not limited to, =NH, =NMe, and =NEt.

Amidine (amidino): —C(=NR)NR₂, wherein each R is an amidine substituent, for example, hydrogen, a $C_{1-7}$ alkyl group, a $C_{3-20}$ heterocyclyl group, or a $C_{5-20}$ aryl group, preferably H or a $C_{1-7}$ alkyl group. Examples of amidine groups include, but are not limited to, —C(=NH)NH₂, —C(=NH)NMe₂, and —C(=NMe)NMe₂.

Cyano (nitrile, carbonitrile): —CN.

Thioether (sulfide): —SR, wherein R is a thioether substituent, for example, a $C_{1-7}$ alkyl group (also referred to as a $C_{1-7}$ alkylthio group), a $C_{3-20}$ heterocyclyl group, or a $C_{5-20}$ aryl group, preferably a $C_{1-7}$ alkyl group. Examples of $C_{1-7}$ alkylthio groups include, but are not limited to, —SCH₃ and —SCH₂CH₃.

Disulfide: —SS—R, wherein R is a disulfide substituent, for example, a $C_{1-7}$ alkyl group, a $C_{3-20}$ heterocyclyl group, or a $C_{5-20}$ aryl group, preferably a $C_{1-7}$ alkyl group (also referred to herein as $C_{1-7}$ alkyl disulfide). Examples of $C_{1-7}$ alkyl disulfide groups include, but are not limited to, —SSCH₃ and —SSCH₂CH₃.

Sulfine (sulfinyl, sulfoxide): —S(=O)R, wherein R is a sulfine substituent, for example, a $C_{1-7}$ alkyl group, a $C_{3-20}$ heterocyclyl group, or a $C_{5-20}$ aryl group, preferably a $C_{1-7}$ alkyl group. Examples of sulfine groups include, but are not limited to, —S(=O)CH₃ and —S(=O)CH₂CH₃.

DETAILED DESCRIPTION

The present invention will now be described with reference to specific embodiments.

Preparation of 3-methyl-3-(phenylthio)butyl acrylate (MPTBA)

(a) Synthesis of 3-methyl-3-(phenylthio)butan-1-ol (1)

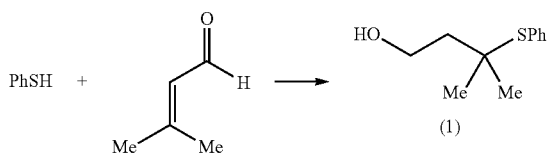

The synthesis of 3-methyl-3-(phenylthio)butan-1-ol (1) is based on the method reported by Vasella et al.; *Helvetica Chimica Acta*, 1995, Vol. 78, pp. 732-757.

To a 1 L 3-neck round-bottomed flask was added (in order): prenal (96.74 g, 1.15 moles), thiophenol (126.68 g, 1.15 moles) and chloroform (250 mL). The apparatus was set-up for reflux and purge-filled with a nitrogen atmosphere. The reaction flask was surrounded with an ice/brine cooling bath and the reaction mixture cooled to ca. 0° C. Triethylamine (4.10 mL, 0.029 moles) was then added to the reaction mixture dropwise over a period of 7 minutes. This addition was accompanied by an exotherm, from −3° C. to +15° C.

After the addition, the cooling bath was removed and the reaction mixture allowed to warm to room temperature whilst being stirred under nitrogen over a period of 4 hours. The reaction mixture was then surrounded with an ice/brine cooling bath and chilled to −5° C. Separately sodium borohydride (17.4 g, 0.46 moles) was dissolved in water (85 mL) and this solution was added dropwise to the reaction mixture under a nitrogen atmosphere over a period of 45 minutes whilst ensuring that the temperature of reaction did not exceed +10° C.

Upon the completion of the aqueous sodium borohydride addition, the reaction mixture was allowed to warm to room temperature. As the reaction proceeded the colour of the reaction changed from pale brown to pale yellow and a gelatinous precipitate deposited from the mixture. The reaction mixture was then stirred at room temperature for a period of 16 hours before the excess sodium borohydride was destroyed by careful dropwise addition of aqueous hydrochloric acid (1M, 345 mL). The resultant mixture was transferred to a 1 L separating funnel and after the aqueous and organic layers had partitioned, the organic layer was separated. The remaining aqueous layer was extracted with chloroform (100 mL) and was then partitioned and separated. The organic layers were combined and extracted with brine (250 mL) before being dried over anhydrous magnesium sulfate for a period of 45 minutes. The drying mixture was filtered and the collected solid washed with chloroform (2×50 mL portions). The filtrate and washings were combined and the chloroform solvent stripped off in vacuo using a rotary evaporator yielding a pale yellow slightly viscous liquid, which was then fractionally distilled in vacuo though a vacuum jacketed 30 cm Vigreux column the main product fraction distilling over at 96-98° C. (0.285 Torr).

Yield: 192 g; appearance: very pale straw coloured liquid. $^1$H NMR [200 MHz, CDCl$_3$]: 1.27 ppm (6H, s, —CH$_3$); 1.78 (2H, t, >CH$_2$); 2.37 (1H, bs, —OH); 3.89 (2H, t, >CH$_2$); 7.30-7.56 (5H, m, ArH).

(b) Synthesis of 3-methyl-3-(phenylthio)butyl acrylate (2)

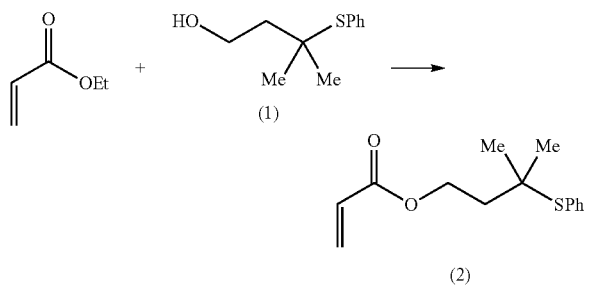

Into a 3-neck round-bottomed flask was placed (in order): N,N'-diphenyl-1,4-phenylenediamine (0.53 g, 2.04×10$^{-3}$ moles), 3-Methyl-3-(phenylthio)butan-1-ol (50.0 g, 0.255 moles) and ethyl acrylate (276 mL, 2.55 moles). The apparatus was then assembled for reactive distillation through a Claisen head and purge-filled with nitrogen gas. The reaction flask was heated to 110-115° C. and after ca. 5 mL of ethyl acrylate had distilled over, titanium(IV) isoproproxide (TPT, 2.26 mL, 7.65×10$^{-3}$ moles) was added to the reaction mixture via syringe in one portion. The rate of distillation immediately increased significantly and the distillate vapour temperature decreased from 99° C. to 90° C. These distillation conditions were maintained for a period of 150 minutes before the apparatus was evacuated by means of a 10 mbar PTFE-diaphragm pump and the remaining ethyl acrylate was stripped from the reaction mixture. The apparatus was then pumped down using a two-stage oil pump and the crude product distilled over at a vapour temperature of 109.5-112° C. (0.18 Torr, appearance: golden liquid, yield: 50.8 g).

The crude product was taken up in n-hexane (300 mL) and extracted with 4×400 mL 1M aqueous hydrochloric acid. For the first two extractions the aqueous layers took on a pronounced blue coloration indicative of the protonation and aqueous solvation of the N,N'-diphenyl-1,4-phenylene-diamine polymerisation inhibitor. The organic layer was then extracted with 2×400 mL portions of brine and then dried over anhydrous magnesium sulfate for a period of 1 hour. The drying solution was then filtered and the collected solid washed with 2×50 mL portions of n-hexane. The filtrate and washings were combined and the n-hexane solvent stripped off in vacuo using a rotary evaporator. The slightly turbid colourless liquid residue was distilled using a short-path Kugelrohr distillation apparatus using microspatula measure of 5,5',6,6'-tetrahydroxy-3,3,3',3'-tetramethyl-1,1'-spirobis-indane as a polymerisation inhibitor. The Kugelrohr oven temperature was 180° C., the vacuum pressure was 0.055 Torr, and the receiver bulb was chilled in a dry-ice/acetone cooling bath to prevent gelation of the distillate.

Yield: 33.5 g. Appearance: colourless liquid. $^1$H NMR [200 MHz, CDCl$_3$]: 1.29 ppm (6H, s, —CH$_3$); 1.87 (2H, t, >CH$_2$); 4.42 (2H, t, >CH$_2$); 5.81 (1H, dd, >C=CHH); 6.10 (1H, q, >C=CHH); 6.39 (1H, d, —C(=O)—CH=CH$_2$), 7.26-7.53 (5H, m, ArH).

Preparation of 2-(2-phenylpropan-2-ylthio)ethyl acrylate (PPTEA)

(a) Synthesis of 2-(2-phenylpropan-2-ylthio)ethanol (3)

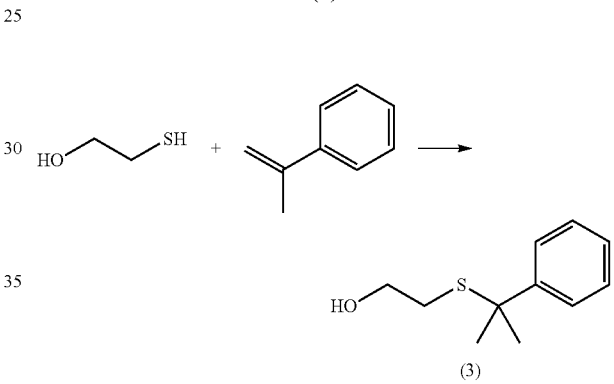

A 1 L 3-neck round-bottomed flask was connected to a double-layer coil condenser (side-arm), B19 stopper (side-arm) and a 125 mL pressure-equalising addition funnel (stoppered, centre-socket). The condenser was then connected to a inline mineral oil bubbler and the apparatus was flushed with nitrogen. α-Methylstyrene (46.0 mL) was dissolved in 70 mL of acetic acid and this solution added to the addition funnel. 2-Mercaptoethanol (37.4 mL) was added to the reaction flask followed by acetic acid (300 mL) and concentrated sulfuric acid (37 drops). The reaction flask was then surrounded with a silicone oil heating bath and heated to 60° C. Once thermally equilibrated the α-methylstyrene solution was added dropwise to the reaction mixture under nitrogen over five hours at an approximate rate of 1 drop every 2 seconds. After completion of the addition the reaction mixture was stirred at 60° C. overnight under nitrogen.

The next day, the heat source was removed and the reaction mixture allowed to cool to room temperature. Triethylamine (10 mL) was then added to the reaction mixture (in order to neutralise the sulfuric acid catalyst) and the acetic acid solvent stripped off in vacuo (bath T: 40-60° C./vacuum: 50 torr gradually reduced to 3 torr) yielding about 100 mL of a slightly turbid colourless liquid in the distillation flask. This liquid was taken up in 300 mL of diethyl ether and this solution transferred to a 1 L separating funnel and this solution extracted with a single portion of saturated aqueous sodium bicarbonate (400 mL) followed by a single portion of brine (400 mL). The layers were then allowed to partition and the lower aqueous layer decanted off. The ethereal layer was then collected and stripped to dryness in vacuo using a rotary evaporator yielding about 100 mL of a colourless liquid. A small aliquot of this crude product was analysed by gas chromatography which indicated the desired product had formed. Separately 36 g of NaOH was dissolved in 140 mL de-ionised water forming a colourless solution and this was CAREFULLY added to the crude product and the resultant immiscible mixture was brought up to reflux under a nitrogen atmosphere for a period of 90 minutes. The reaction mixture was then allowed to cool and was transferred to a 500 mL separating funnel. Diethyl ether (100 mL) and brine (50 mL) were added to the separating funnel which was then shaken for 2 minutes. The layers were allowed to partition and the lower aqueous layer was decanted off and discarded. The ethereal layer was then extracted with 3×175 mL portions of brine. The ethereal layer was then collected and dried over anhydrous magnesium sulfate for a period of 30 minutes. The drying mixture was then filtered and the collected solid washed with 3×40 mL portions of diethyl ether. The filtrate and washings were combined and stripped to dryness in vacuo using a rotary evaporator. The resultant yellow liquid was then fractionally distilled in vacuo through a 30 cm column containing 4 mm Fenske rings:

FRACTION #1: 98.0 deg C. (0.33 TORR)—Colourless liquid [Pre-fraction→discarded]

FRACTION #2: 98.0-98.5 deg C. (0.33 torr)—Colourless liquid

FRACTION #3: 98.5-99.5 deg C. (0.365 torr)—Colourless liquid

FRACTION #4: 99.5-100.5 deg C. (0.345 torr)—Colourless liquid

FRACTION #5: 101-137 deg C. (0.32-0.45 torr)—Colourless to very pale yellow liquid (Small amount of cross-fraction going to higher boiling fraction—discarded).

Fractions 2-4 were analysed by gas chromatography which indicated that fractions 3 and 4 were sufficiently pure to be combined with an α-methylstyrene dimer content <0.15% but fraction 2 with an α-methylstyrene dimer content of 0.30% required further purification.

Fraction 2 comprising 14.5 g of material was then analysed by TLC (20% EtOAc/80% n-hexane) against a pure sample of α-methylstyrene dimer, the (3) product ran with an $R_f$ of 0.34 whereas the α-methylstyrene dimer ran near the solvent front with an $R_f$ of 0.90. Fraction 2 was then purified by dry-column flash chromatography using the following parameters: (i) Fraction 2 pre-loaded onto 17 g of Merck 60 (15-40 µm) silica-gel; (ii) Column size: 80 mm diameter/60 mm depth; (iii) Merck 60 (15-40 µm) silica gel; (iv) Fraction volumes: 100 mL; (v) Time per fraction: 3.00 minutes; (vi) Elution gradient: 100-66% n-hexane (in 2% increments)/0-34% EtOAc (in 2% increments), a total of 18 fractions. Fractions 10-14 "foamed" on exiting the column. Fractions 10-17 were analysed by gas chromatography which indicated that most of the α-methylstyrene dimer had been effectively removed by the column purification. Fractions 10-16 were combined and stripped to dryness in vacuo (rotary evaporator) and combined with the earlier distillation fractions' 3 and 4 and this combined material dried in vacuo (oil immersion pump) overnight at room temperature. The yield of the dried, purified product was recorded the following day.

Yield: 45.8 g, colourless liquid. $^1$H NMR [200 MHz, CDCl$_3$]: 1.72 ppm (6H, s, —CH$_3$); 2.10 (1H, t, —OH); 2.45 (2H, t, —SCH$_2$); 3.40 (2H, q, —OCH$_2$); 7.15-7.58 (5H, m, ArH).

(b) Synthesis of 2-(2-phenylpropan-2-ylthio)ethyl acrylate (4) [via reverse transesterification]

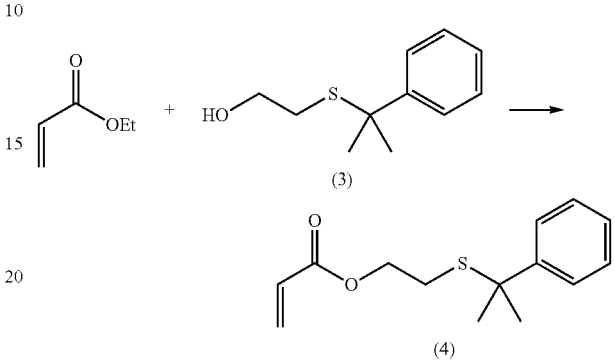

Into a 3-neck 250 mL round-bottomed flask were weighed, in the following order: 2-(2-phenylpropan-2-ylthio)ethanol (30.0 g, 0.1528 moles), N,N'-diphenyl-1,4-phenylene diamine (0.318 g, 1.2224×10$^{-3}$ moles) and ethyl acrylate (122.40 g, 1.2224 moles). The apparatus was then assembled in a reactive distillation arrangement before being purged with N$_2$ (g). The Claisen head of the distillation apparatus was wrapped with Al-foil/glass wool. The reaction flask was then heated to 120° C., by use of a silicone heating oil bath, and once the ethyl acrylate (Bpt: 99° C.) started to distil over tetrapropoxytitanate (TPT) (1.04 mL, 0.999 g, 3.5144×10$^{-3}$ moles) was added to the reaction mixture via a 2.50 mL Hamilton gastight syringe. The distillation rate immediately increased significantly and the distillation vapour temperature decreased from 98° C. to ca. 80° C.

The heating temperature of 120° C. was maintained for 30 mins before being increased to 140° C. for a further 60 mins, during this period the distillate vapour temperature increased from 80° C. to 98° C. The hot silicone oil bath was then removed and exchanged for a silicone oil bath at room temperature. The apparatus was then evacuated by means of a 10 mbar PTFE-diaphragm pump and the remaining ethyl acrylate stripped off as the reaction flask was incrementally heated to a temperature of 100° C. The flask was then immediately switched to evacuation by means of a two-stage oil pump (0.12 Torr) and the crude product distilled over at a vapour temperature of 100-106° C. as the silicone heating oil bath was heated from 100° C. to 140° C. The crude product was an optically clear colourless liquid (yield: 33.7 g). The crude product was dissolved in 200 mL n-hexane and then extracted with 2×200 mL portions of HCl (aq, 2M) and 2×200 mL portions of de-ionised water. The organic layer was partitioned and separated and then dried over anhydrous magnesium sulfate for a period of 45 minutes. The drying agent was then filtered off and washed with 2×30 mL portions of n-hexane. The filtrate and washing were combined and the n-hexane solvent stripped off using a rotary evaporator. The pale yellow liquid residue was then doubly distilled in vacuo using a Kugelrohr short-path distillation apparatus (oven temperature: 180° C., vacuum pressure: 0.13 torr) with the receiver flask, in each instance, cooled by means of a dry-ice/acetone bath.

Yield: 31.30 g (colourless liquid). $^1$H NMR [300 MHz, CDCl$_3$]: 1.72 ppm (6H, s, —CH$_3$); 2.51 (2H, t, —SCH$_2$); 4.03 (2H, t, —OCH$_2$); 5.80 (1H, d, >C=CHH); 6.07 (1H, q, >C=CHH); 6.37 (1H, d, —C(=O)—CH=CH$_2$); 7.18-7.57 (5H, m, ArH).

(c) Synthesis of 2-(2-phenylpropan-2-ylthio)ethyl acrylate (4) [via non-aqueous Schotten-Baumann esterification]

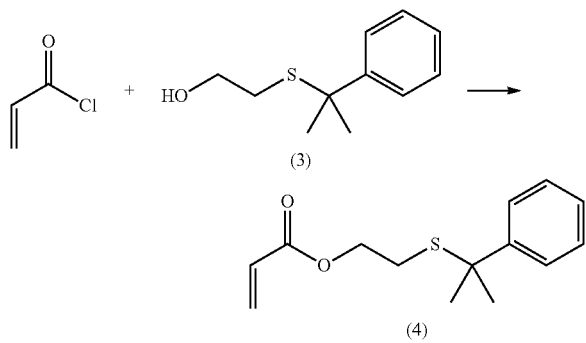

2-(2-Phenylpropan-2-ylthio)ethanol (45.0 g, 229 mmol) was weighed into a 1 L 3-neck round-bottomed flask which was then attached to a 125 mL pressure-equalising funnel (centre-socket), a Suba-seal (side-arm) and a double layer coil condenser (side-arm) which was connected in turn to a nitrogen-vacuum manifold. The apparatus was then purge-filled with nitrogen three times. Dichloromethane (anhydrous, 300 mL) was then cannula transferred into the reaction flask. DIPEA (anhydrous, 60 mL) was then added to the reaction solution using a 20 mL gastight syringe (3×20 mL transfers). Freshly distilled acryloyl chloride (22.35 mL) was then placed in the pressure-equalising addition funnel. The reaction flask was then surrounded with a dry-ice/acetone cooling bath and the reaction mixture cooled to a temperature of −77° C. The acryloyl chloride was then added slowly dropwise to the chilled reaction mixture under nitrogen over a period of 90 minutes (ca. 1 drop every 2 seconds). The reaction mixture was then stirred in the cooling bath under nitrogen overnight and allowed to warm slowly to room temperature. Next day the reaction flask was surrounded with a water/ice cooling bath and methanol (50 mL) was added to the pressure-equalising addition funnel. The reaction mixture was cooled to <5° C. and the methanol then added dropwise over a period of 30 minutes in order to quench the excess acryloyl chloride. The reaction mixture was then allowed to warm to room temperature before being extracted with 1×300 mL portion of 1M HCl (aq) and 2×300 mL portions of brine. The organic layer was then partitioned and separated and then dried over anhydrous magnesium sulfate for a period of 1 hour. The drying mixture was then filtered and the collected solid washed with 3×40 mL portions of dichloromethane. The filtrate and washings were combined and then CAREFULLY stripped to dryness in vacuo (rotary evaporator) at a bath temperature of 25° C. The resultant orange liquid (with a small quantity of white "gel-like" material on the walls of the evaporation flask, presumably polymer) was distilled in vacuo through a Claisen head with a spatula measure of 5,5',6,6'-tetrahydroxy-3,3,3',3'-tetramethyl-1,1-spirobisindane inhibitor added to the distillation mixture.

FRACTION #1: 25-116 deg C. (0.705 torr): PRE-FRACTION (DISCARDED).
FRACTION #2: 116-122 deg C. (0.72-0.86 torr): PALE YELLOW LIQUID (tainted with some 'splash over' from the distillation pot).
FRACTION #3: 122-123 deg C. (0.86 torr): COLOURLESS LIQUID.

Fraction 2 was tainted with some 'splash over' from the distillation pot and so required redistilling. Fraction #1 was discarded whilst fractions' 2 & 3 were combined and re-distilled in the presence of a spatula measure of 5,5',6,6'-tetrahydroxy-3,3,3',3'-tetramethyl-1,1-spirobisindane inhibitor through a 5 cm Vigreux column in vacuo, the distillate coming over in a single colourless fraction at 105-112.5° C. (0.350 torr).

Yield: 49.95 g, colourless liquid. $^1$H NMR [300 MHz, CDCl$_3$]: 1.72 ppm (6H, s, —CH$_3$); 2.51 (2H, t, —SCH$_2$); 4.03 (2H, t, —OCH$_2$); 5.80 (1H, d, >C=CHH); 6.07 (1H, q, >C=CHH); 6.37 (1H, d, —C(=O)—CH=CH$_2$); 7.18-7.57 (5H, m, ArH).

Analytical Methods

Analytical methods for assessing the physical properties of the polymers prepared are described below.

Swell Factor

The swell factor of the polymer is a measure of the degree the material expands in size when hydrated. A sample of polymer of accurately determined dimensions was placed in saline and allowed to swell until it reached a steady maximum dimension. The increase in size of the sample in any axis is expressed as a function of the original dimension.

Refractive Index

The refractive index of the polymer was determined using a refractometer such as the Atago R500 or an Abbe type instrument such as a Bellingham & Stanley 70/80 unit.

Mechanical Properties

The mechanical properties of the polymer were determined by tensile testing of the material using a Zwick Z0.5 tensiometer equipped with a KAD-Z 100N load cell. The jaws of the tensiometer were set to 10 mm separation, and the test speed to 10 mm/min.

Test strips were cut from polymer films and individually mounted between the jaws of the tensiometer. The test strip was held under tension, and the force applied was gradually increased until the sample broke. The modulus of elasticity was determined from a graphical plot of stress against strain over the elastic region of the curve. For each material a number of strips were tested and the results averaged.

Polymerisable Compositions, Polymers and Polymer Discs

Example 1

A polymerisable composition comprising MPTBA (1.433 g), 2-hydroxyethyl methacrylate (HEMA) (0.3772 g), N,N-dimethylformamide (DMF) (0.414 g), 1,2-ethyleneglycol dimethacrylate (EGDMA) (0.0566 g), 2-(4'-benzoyl-3'-hydroxyphenoxy)ethyl acrylate (AEHB) (0.0189 g) and azobisisobutyronitrile (AIBN) (2.3 mg) was homogenised by vigorous magnetic stirring in a 4 mL sample vial for 15 minutes. Separately four single-impression conical-frustum shaped polypropylene button moulds (lower base diameter: 13.80 mm; upper base diameter: 14.05 mm; upper-lower base depth: 3.00 mm) were covered with polypropylene lid-stock with an aperture left open to permit the filling of the moulds. Each of the moulds was then filled with a portion of the composition. All bubbles were purged from the filled mould and it was heat-sealed. The four moulds were placed in a 2 L aqueous polymerisation bath which had been pre-heated to an equilibrium temperature of 57° C. The moulds were maintained at a temperature of 57° C. in the aqueous polymerisation bath for a period of 19 hours.

The polymerisation bath was allowed to cool to room temperature before the four single-impression button moulds were removed, rinsed with tepid water and carefully hand-dried. The lid-stock about each of the button impressions on the four moulds was pierced without cutting the actual moulds themselves. The four moulds were then placed in a dry-ice cabinet for a period of 5 minutes before being removed. The lid-stock was then immediately peeled away from the mould and the conical-frustum shaped polymer discs extruded. The polymer discs were transferred to a Soxhlet extraction apparatus and extracted with acetonitrile, under an inert nitrogen atmosphere, for a period of 24 hours. The extraction apparatus was then allowed to cool to room temperature and the four polymer discs removed and dried in air for a period of 4 hours at room temperature prior to being dried/annealed in vacuo using a dry-ice/isopropanol cold-trapped vacuum oven and the following program:

RAMP: to 30° C.; HOLD: 30° C. for 4 hours; RAMP: 30° C. to 110° C. at 10° C. per hour; HOLD: 110° C. for 6 hours; RAMP: 110° C. to 20° C. at 15° C. per hour.

The lowest pressure obtained was <0.05 Torr at the completion of the annealing cycle. The polymer discs removed from the vacuum oven were hard, transparent and colourless. Four parallel convex lens shapes, with a diameter of 8.50 mm and a centre thickness of 0.30 mm, were immediately lathe cut from these polymer discs.

The lenses were then swelled in physiological saline and were colourless, optically clear, soft, tack-free and easily foldable.

$n_D^{35°\ C.}$(hydrated)=1.5520,

Linear swell factor (35° C.)=1.0118.

The IOL lens shapes may be rolled at 35° C., and inserted into narrow tubes of approximately 3 mm internal diameter. The rolled up lenses and tubes may then be placed in an environmental cabinet at 35° C. for a period of time to simulate the conditions in a human eye. When the lenses and tubes have had sufficient time to reach equilibrium under these conditions, the lenses are removed from the tubes. It is desirable that the IOL portion spontaneously unrolls and assumes its original bi-convex shape in less than one minute. If the IOL portion meets this requirement, then this test demonstrates that the IOL portions were not damaged by rolling and storage, and suggests that they are suitable for use in cataractous lens replacement surgery.

Example 2

The same fabrication and processing procedure was followed as in Example 1 but the following polymerisable composition was employed: MPTBA (1.405 g), N,N-dimethylacrylamide (DMA) (0.3772 g), DMF (0.414 g), EGDMA (0.0849 g), AEHB (0.0189 g) and AIBN (2.3 mg). The hydrated lathe-machined parallel convex lenses were colourless, optically clear, soft, tack-free and easily foldable.

$n_D^{35°\ C.}$(hydrated)=1.5450,

Linear swell factor (35° C.)=1.0235.

Example 3

The same fabrication and processing procedure was followed as Example 1 but the following polymerisable composition was employed: 2-(2-phenylpropan-2-ylthio)ethyl acrylate (PPTEA) (1.395 g), HEMA (0.377 g), DMF (0.414 g), EGDMA (0.057 g), 2-[3'-2'H-benzotriazol-2'-yl)-4'-hydroxyphenyl]ethyl methacrylate (BTPEM) (0.057 g) and AIBN (2.3 mg). The hydrated lathe-machined parallel convex lenses were colourless, optically clear, soft, tack-free and easily foldable.

$n_D^{35°\ C.}$(hydrated)=1.5558,

Linear swell factor (35° C.)=1.0118.

Example 4

The same fabrication and processing procedure was followed as Example 1, but the following polymerisable composition was used: PPTEA (1.019 g), HEMA (0.754 g), DMF (0.414 g), EGDMA (0.057 g), BTPEM (0.056 g) and AIBN (2.3 mg). The resulting hydrated lathe-machined parallel convex lenses were colourless, optically clear, soft, tack-free and easily foldable.

$n_D^{35°\ C.}$(hydrated)=1.5365

Linear swell factor (35° C.)=1.0235

Example 5

The same fabrication and processing procedure was followed as Example 1, using the following polymerisable composition: PPTEA (1.019 g), HEMA (0.754 g), DMF (0.414 g), EGDMA (0.057 g), AEHB (0.056 g) and AIBN (2.3 mg). The resulting hydrated lathe-machined parallel convex lenses were colourless, optically clear, soft, tack-free and easily foldable.

$n_D^{35°\ C.}$(hydrated)=1.5355

Linear swell factor (35° C.)=1.0235

Example 6

The same fabrication and processing procedure was followed as Example 1 but the following polymerisable composition was used: PPTEA (1.001 g), DMA (0.7544 g), DMF (0.414 g), EGDMA (0.0754 g), BTPEM (0.0557 g) and AIBN (2.3 mg). Post hydration the lathe-machined parallel convex lenses were colourless, optically clear, soft and easily foldable though rather tacky to the touch.

$n_D^{35°\ C.}$(hydrated)=1.5090

Linear swell factor (35° C.)=1.0753

Table 1 is a summary of the components included in the polymerisable compositions in the examples above.

TABLE 1

Summary of the polymerised compositions of Examples 1 to 6.

| Monomer (% wt) | Example No. | | | | | |
|---|---|---|---|---|---|---|
| | 1 | 2 | 3 | 4 | 5 | 6 |
| MPTBA | 62.32 | 61.09 | — | — | — | — |
| PPTEA | — | — | 60.68 | 44.31 | 44.31 | 43.50 |
| HEMA | 16.40 | — | 16.40 | 32.80 | 32.80 | — |
| DMA | — | 16.40 | — | — | — | 32.80 |
| EGDMA | 2.46 | 3.69 | 2.46 | 2.46 | 2.46 | 3.28 |
| AEHB | 0.82 | 0.82 | — | — | 2.43 | — |
| BTPEM | — | — | 2.46 | 2.43 | — | 2.42 |
| Diluent (% wt): DMF | 18.00 | 18.00 | 18.00 | 18.00 | 18.00 | 18.00 |
| Initiator (% wt): AIBN | 0.10 | 0.10 | 0.10 | 0.10 | 0.10 | 0.10 |
| Swell Factor | 1.0118 | 1.0235 | 1.0118 | 1.0235 | 1.0235 | 1.0753 |

TABLE 1-continued

Summary of the polymerised compositions of Examples 1 to 6.

| Monomer (% wt) | Example No. | | | | | |
|---|---|---|---|---|---|---|
| | 1 | 2 | 3 | 4 | 5 | 6 |
| Refractive Index | 1.5520 | 1.5450 | 1.5558 | 1.5365 | 1.5355 | 1.5090 |

Example 7

For compositions that are difficult to lathe cut at room temperature it is desirable to produce a polymer in the form of a thin film in order that its properties can be investigated.

A thin polymer film was produced through polymerisation of a composition as follows: PPTEA (2.000 g), ethoxylated bisphenol A (1EO/Phenol) diacrylate (BPADA) (0.06 g), BTPEM (0.060 g) and AIBN (0.010 g). Two glass plates were coated with a polyethylene sheet and a 0.5 mm thick cell was created between the polyethylene sheets using a polyethylene gasket. The coated faces of the glass sheets were clipped together using springclips with a G21 syringe needle being placed between the gasket and the polyethylene sheets. The cavity was then filled through the needle using a syringe. Once the cavity was filled the syringe needle was removed, a final clip was used to seal the mould and the assembly was placed in an oven at 60° C. for 18 hours followed by 90° C. for 5 hours. The moulds were allowed to cool to room temperature before the film was removed from the mould. The polymer films were annealed in vacuo using a dry-ice/isopropanol cold-trapped vacuum oven and the following program:

RAMP: to 30° C.; HOLD: 30° C. for 4 hours; RAMP: 30° C. to 110° C. at 10° C. per hour; HOLD: 110° C. for 6 hours; RAMP: 110° C. to 20° C. at 15° C. per hour.

The resulting film was colourless, optically clear, soft, easily foldable and slightly tacky to the touch. The material did not swell in saline and did not develop glistenings after prolonged storage in saline at 37° C. This material had a modulus of around 0.7 MPa and an elongation to break of around 100%.

Example 8

The same fabrication and processing procedure was followed as example 7 but the following polymerisable composition was used PPTEA (2.000 g), Ethylene Glycol dimethacrylate (EGDMA) (0.060 g), BTPEM (0.060 g) and AIBN (0.010 g). The resulting film was colourless, optically clear, soft and easily foldable. The material did not swell in saline and did not develop glistenings after prolonged storage in saline at 37° C. This material had a modulus around 0.61 MPa and an elongation of 123%.

Example 9

The same fabrication and processing procedure was followed as example 7 but the following polymerisable composition was used PPTEA (2.000 g), Di-vinyl benzene (DVB) (0.060 g), BTPEM (0.060 g) and AIBN (0.010 g). The resulting film was colourless, optically clear, soft and easily foldable. The material did not swell in saline and did not develop glistenings after prolonged storage in saline at 37° C. This material had a modulus around 1.29 MPa and an elongation of 66%.

Example 10

The same fabrication and processing procedure was followed as example 7 but the following polymerisable composition was used PPTEA (2.000 g), Triallyl-triazine-trione (TAIC) (0.060 g), BTPEM (0.060 g) and AIBN (0.010 g). The resulting film was colourless, optically clear, soft and easily foldable. The material did not swell in saline and did not develop glistenings after prolonged storage in saline at 37° C. This material had a modulus around 0.32 MPa and an elongation of 190%.

Example 11

The same fabrication and processing procedure was followed as example 7 but the following polymerisable composition was used PPTEA (2.000 g), polypropylene glycol dimethacrylate (PPGDMA) (0.060 g), BTPEM (0.060 g) and AIBN (0.010 g). The resulting film was colourless, optically clear, soft and easily foldable. The material did not swell in saline and did not develop glistenings after prolonged storage in saline at 37° C. This material had a modulus around 0.43 MPa and an elongation of 117%.

Example 12

The same fabrication and processing procedure was followed as example 7 but the following polymerisable composition was used PPTEA (2.000 g), hexanediol diacrylate (HDDA) (0.060 g), BTPEM (0.060 g) and AIBN (0.010 g). The resulting film was colourless, optically clear, soft and easily foldable. The material did not swell in saline and did not develop glistenings after prolonged storage in saline at 37° C. This material had a modulus around 0.82 MPa and an elongation of 66%.

Example 13

The same fabrication and processing procedure was followed as example 7 but the following polymerisable composition was used: PPTEA (1.7700 g), styrene (0.1500 g), DVB (0.020 g), BTPEM (0.060 g) and AIBN (0.010 g). The resulting film was colourless, optically clear, soft and easily foldable. The material did not swell in saline and did not develop glistenings after prolonged storage in saline at 37° C. This material had a modulus around 0.68 MPa and an elongation of 175%.

Example 14

The same fabrication and processing procedure was followed as example 7 but the following polymerisable composition was used: PPTEA (1.7200 g), styrene (0.2000 g), DVB (0.020 g), BTPEM (0.060 g) and AIBN (0.010 g). The resulting film was colourless, optically clear, soft and easily foldable. The material did not swell in saline and did not develop glistenings after prolonged storage in saline at 37° C. This material had a modulus around 1.11 MPa and an elongation of 181%.

Example 15

The same fabrication and processing procedure was followed as example 7 but the following polymerisable composition was used: PPTEA (1.6700 g), styrene (0.2500 g), DVB (0.020 g), BTPEM (0.060 g) and AIBN (0.010 g). The resulting film was colourless, optically clear, soft and easily foldable. The material did not swell in saline and did not develop glistenings after prolonged storage in saline at 37° C. This material had a modulus around 1.57 MPa and an elongation of 187%.

Table 2 is a summary of the components included in the polymerisable compositions in the examples above.

TABLE 2

Summary of the polymerisable compositions in Examples 7 to 15.

| Monomer (% wt) | 7 | 8 | 9 | 10 | 11 | 12 | 13 | 14 | 15 |
|---|---|---|---|---|---|---|---|---|---|
| PPTEA | 94.245 | 94.245 | 94.245 | 94.245 | 94.245 | 94.245 | 88.50 | 86.00 | 83.50 |
| BPADA | 2.926 | | | | | | | | |
| EGDMA | | 2.926 | | | | | | | |
| DVB | | | 2.926 | | | | 1.0 | 1.0 | 1.0 |
| TAIC | | | | 2.926 | | | | | |
| PPGDMA | | | | | 2.926 | | | | |
| HDDA | | | | | | 2.926 | | | |
| Styrene | | | | | | | 7.5 | 10.0 | 12.5 |
| BTPEM | 2.829 | 2.829 | 2.829 | 2.829 | 2.829 | 2.829 | 3.00 | 3.00 | 3.00 |
| AIBN (% wt) | 0.471 | 0.471 | 0.471 | 0.471 | 0.471 | 0.471 | 0.500 | 0.500 | 0.500 |
| Modulus MPa | 0.70 | 0.61 | 1.29 | 0.32 | 0.43 | 0.82 | 0.68 | 1.11 | 1.57 |
| Elongation to break % | 100 | 123 | 66 | 190 | 117 | 66 | 175 | 181 | 187 |
| $n_D^{20°\,C.}$ | 1.5740 | 1.5743 | 1.5765 | 1.5748 | 1.5720 | 1.5731 | 1.5798 | 1.5797 | 1.5813 |

It will be apparent to one of ordinary skill that the monomer of the invention may be used to produce both hydrophilic and non-hydrophilic polymers. Such systems can be simple, with just a single cross-linking co-monomer, or extremely complex, with a large number of co-monomers.

REFERENCES

Matsuda et al. Journal of Macromolecular Science, Part A, Volume 36, Issue 9, 1999, pp. 1271-1288. Novel Thiophene Methacrylates for Materials of High Refractive Index.
U.S. Pat. No. 3,799,972
U.S. Pat. No. 5,674,960
U.S. Pat. No. 5,922,821
WO 96/40303
WO 00/79312
U.S. Pat. No. 5,290,892
U.S. Pat. No. 5,403,901
U.S. Pat. No. 5,674,960
U.S. Pat. No. 5,861,031
Vasella et al.; Helvetica Chimica Acta, 1995, Vol. 78, pp. 732-757
U.S. Pat. No. 6,780,899

The invention claimed is:

1. A monomer for a polymerizable composition, the monomer being selected from the group consisting of compounds having formula (I) and compounds having formula (Ia):

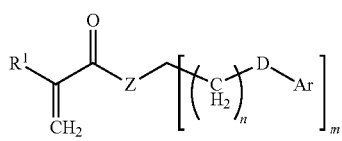

(I)

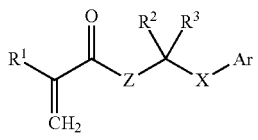

(Ia)

wherein D is:

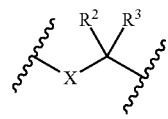

and

R$^1$ is hydrogen or a methyl group;
Z is O or N—R$^4$, where R$^4$ is hydrogen or $C_{1-10}$ alkyl;
m is an integer from 1 to 3;
n is an integer from 0 to 6;
R$^2$ and R$^3$ are independently selected from $C_{1-10}$ alkyl, $C_{3-10}$ cycloalkyl, $C_{6-37}$ aryl ether, an optionally substituted $C_{4-36}$ heterocyclyl, $C_{1-7}$ alkoxy, $C_{5-36}$ aryloxy, and $C_{2-11}$ alkyl ether;
X is sulphur;
Ar is an optionally substituted $C_{5-36}$ aryl group;
wherein the optional substituents for when Ar is an optionally substituted $C_{5-36}$ aryl group are independently selected from halogen atom, $C_{1-10}$ alkyl, $C_{3-10}$ cycloalkyl, $C_{5-36}$ aryl, $C_{5-37}$ aryl ether, $C_{1-7}$ alkoxy, $C_{6-37}$ aryl thioether, an optionally substituted $C_{4-36}$ heterocyclyl, $C_{2-11}$ alkyl ether, $C_{2-11}$ alkyl thioether, $C_{5-36}$ aryloxy, $C_{5-36}$ arylsulfide, $C_{6-38}$ arylalkyl and an optionally substituted $C_{5-38}$ heterocyclyl-alkyl group.

2. A polymerizable composition comprising:
a crosslinking monomer having a minimum of two unsaturated functional groups; and
a monomer selected from the group consisting of compounds having formula (I) and compounds having formula (Ia):

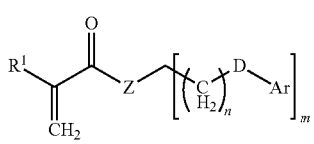

(I)

-continued

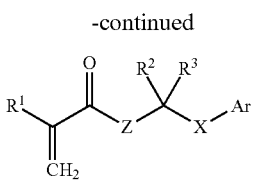
(Ia)

wherein D is:

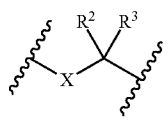

and
R$^1$ is hydrogen or a methyl group;
Z is O or N—R$^4$, where R$^4$ is hydrogen or C$_{1-10}$ alkyl;
m is an integer from 1 to 3;
n is an integer from 0 to 6;
R$^2$ and R$^3$ are independently selected from C$_{1-10}$ alkyl, C$_{3-10}$ cycloalkyl, C$_{5-36}$ aryl, C$_{6-37}$ aryl ether, an optionally substituted C$_{4-36}$ heterocyclyl, C$_{1-7}$ alkoxy, C$_{5-36}$ aryloxy, and C$_{2-11}$ alkyl ether;
X is oxygen or sulphur;
Ar is an optionally substituted C$_{5-36}$ aryl group;
wherein the optional substituents for when Ar is an optionally substituted C$_{5-36}$ aryl group are independently selected from halogen atom, C$_{1-10}$ alkyl, C$_{3-10}$ cycloalkyl, C$_{5-36}$ aryl, C$_{5-37}$ aryl ether, C$_{1-7}$ alkoxy, C$_{6-37}$ aryl thioether, an optionally substituted C$_{4-36}$ heterocyclyl, C$_{2-11}$ alkyl ether, C$_{2-11}$ alkyl thioether, C$_{5-36}$ aryloxy, C$_{5-36}$ arylsulfide, C$_{6-38}$ arylalkyl and an optionally substituted C$_{5-38}$ heterocyclyl-alkyl group.

3. A blank for an ophthalmic lens, the blank being formed from a polymer obtained from a polymerizable composition comprising a monomer selected from the group consisting of compounds having formula (I) and compounds having formula (Ia):

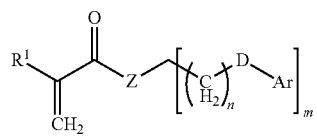
(I)

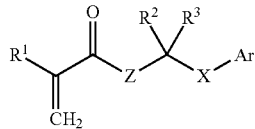
(Ia)

wherein D is:

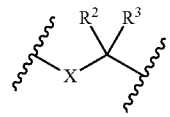

and
R$^1$ is hydrogen or a methyl group;
Z is O or N—R$^4$, where R$^4$ is hydrogen or C$_{1-10}$ alkyl;
m is an integer from 1 to 3;
n is an integer from 0 to 6;
R$^2$ and R$^3$ are independently selected from C$_{1-10}$ alkyl, C$_{3-10}$ cycloalkyl, C$_{5-36}$ aryl, C$_{6-37}$ aryl ether, an optionally substituted C$_{4-36}$ heterocyclyl, C$_{1-7}$ alkoxy, C$_{5-36}$ aryloxy, and C$_{2-11}$ alkyl ether;
X is oxygen or sulphur;
Ar is an optionally substituted C$_{5-36}$ aryl group;
wherein the optional substituents for when Ar is an optionally substituted C$_{5-36}$ aryl group are independently selected from halogen atom, C$_{1-10}$ alkyl, C$_{3-10}$ cycloalkyl, C$_{5-36}$ aryl, C$_{5-37}$ aryl ether, C$_{1-7}$ alkoxy, C$_{6-37}$ aryl thioether, an optionally substituted C$_{4-36}$ heterocyclyl, C$_{2-11}$ alkyl ether, C$_{2-11}$ alkyl thioether, C$_{5-36}$ aryloxy, C$_{5-36}$ arylsulfide, C$_{6-38}$ arylalkyl and an optionally substituted C$_{5-38}$ heterocyclyl-alkyl group.

4. An ophthalmic lens formed from a polymer obtained from a polymerizable composition comprising a monomer selected from the group consisting of compounds having formula (I) and compounds having formula (Ia):

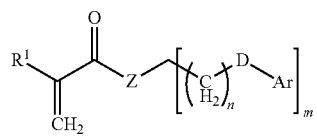
(I)

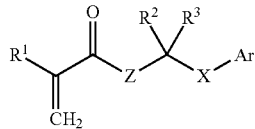
(Ia)

wherein D is:

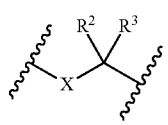

and
R$^1$ is hydrogen or a methyl group;
Z is O or N—R$^4$, where R$^4$ is hydrogen or C$_{1-10}$ alkyl;
m is an integer from 1 to 3;
n is an integer from 0 to 6;
R$^2$ and R$^3$ are independently selected from C$_{1-10}$ alkyl, C$_{3-10}$ cycloalkyl, C$_{5-36}$ aryl, C$_{6-37}$ aryl ether, an optionally substituted C$_{4-36}$ heterocyclyl, C$_{1-7}$ alkoxy, C$_{5-36}$ aryloxy, and C$_{2-11}$ alkyl ether;
X is oxygen or sulphur;
Ar is an optionally substituted C$_{5-36}$ aryl group;
wherein the optional substituents for when Ar is an optionally substituted C$_{5-36}$ aryl group are independently selected from halogen atom, C$_{1-10}$ alkyl, C$_{3-10}$ cycloalkyl, C$_{5-36}$ aryl, C$_{5-37}$ aryl ether, C$_{1-7}$ alkoxy, C$_{6-37}$ aryl thioether, an optionally substituted C$_{4-36}$ heterocyclyl, C$_{2-11}$ alkyl ether, C$_{2-11}$ alkyl thioether, C$_{5-36}$ aryloxy, C$_{5-36}$ arylsulfide, C$_{6-38}$ arylalkyl and an optionally substituted C$_{5-38}$ heterocyclyl-alkyl group.

5. The ophthalmic lens of claim 4, wherein the ophthalmic lens is an intraocular lens.

* * * * *